(12) United States Patent
Lei

(10) Patent No.: US 9,713,565 B2
(45) Date of Patent: Jul. 25, 2017

(54) VIRGINAL REJUVENATION APPARATUS AND METHOD

(71) Applicant: Chongqing Derma Optic&Electronic Technique Co., Ltd., Chongqing (CN)

(72) Inventor: Xiaobing Lei, Chongqing (CN)

(73) Assignee: CHONGQING PENINSULA MEDICAL TECHNOLOGY CO., LTD., Chongqing (CN)

( * ) Notice: Subject to any disclaimer, the term of this patent is extended or adjusted under 35 U.S.C. 154(b) by 0 days.

(21) Appl. No.: 14/675,733

(22) Filed: Mar. 31, 2015

(65) Prior Publication Data

US 2015/0366747 A1 Dec. 24, 2015

(30) Foreign Application Priority Data

Jun. 20, 2014 (CN) .......................... 2014 1 0279768
Jun. 20, 2014 (CN) .......................... 2014 1 0280144
Dec. 19, 2014 (CN) .......................... 2014 1 0793852

(51) Int. Cl.
| | |
|---|---|
| A61H 1/00 | (2006.01) |
| A61H 19/00 | (2006.01) |
| A61N 1/32 | (2006.01) |
| A61F 7/00 | (2006.01) |
| A61F 7/02 | (2006.01) |

(52) U.S. Cl.
CPC ............ *A61H 19/44* (2013.01); *A61N 1/328* (2013.01); *A61F 7/007* (2013.01); *A61F 7/02* (2013.01); *A61F 2007/005* (2013.01); *A61F 2007/0056* (2013.01); *A61F 2007/0086* (2013.01); *A61F 2007/0087* (2013.01); *A61F 2007/0096* (2013.01); *A61H 2201/0153* (2013.01); *A61H 2201/0214* (2013.01); *A61H 2201/0242* (2013.01); *A61H 2201/10* (2013.01); *A61H 2201/5043* (2013.01); *A61H 2201/5058* (2013.01); *A61H 2201/5082* (2013.01)

(58) Field of Classification Search
CPC ............................... A61H 19/40; A61H 19/44
USPC ................................................... 607/138, 96
See application file for complete search history.

(56) References Cited

U.S. PATENT DOCUMENTS

| | | | | |
|---|---|---|---|---|
| 2004/0210214 | A1* | 10/2004 | Knowlton | A61B 18/14 606/41 |
| 2009/0030266 | A1* | 1/2009 | Treanor | A61N 1/36007 600/30 |
| 2011/0230794 | A1* | 9/2011 | van Groningen | A61B 8/546 601/2 |

* cited by examiner

*Primary Examiner* — Nadia A Mahmood
(74) *Attorney, Agent, or Firm* — Syncoda LLC; Feng Ma; Junjie Feng

(57) ABSTRACT

A radio-frequency apparatus is provided for vaginal tightening. The apparatus includes a main engine, a connection device, an applicator, and a negative plate, wherein the applicator includes a hand-held component and a treatment plug. The treatment plug has multiple RF electrodes distributed thereon, and has a size similar to the target tissue such that no movement is necessary during treatment. A controller is employed to connect a RF electrode driving circuit, trigger an electrode driving circuit conduction at a preset frequency as an output RF excitation source. Uneven RF current electrode treatment distribution can thus be resolved by using the RF electrode driving circuit to drive the conduction between the RF electrode and the RF source, at the same time by adopting multiple sets of RF electrode conduction for RF electrode configuration treatment, to ensure uniform distribution between each group of RF electrode currents.

19 Claims, 22 Drawing Sheets

VIRGINAL REJUVENATION APPARATUS AND METHOD

CROSS-REFERENCE TO RELATED APPLICATIONS

The present application is a continuation of, and claims priority to, Chinese Patent Application Nos. CN 201410279768.7 filed on Jun. 20, 2014 (published as CN104013466A on Sep. 3, 2014), CN 201410280144.7 filed on Jun. 20, 2014 (published as CN104013467A on Sep. 3, 2014), and CN 201410793852.0 filed on Dec. 19, 2014 (published as CN104434302A on Mar. 25, 2015). The disclosures of these applications are hereby incorporated by reference in their entirety.

BACKGROUND

Skin rejuvenation is widely used on body surfaces, such as face and body, etc. Recently, skin care has extended to hair removal for Bikini lines, external genital plastic surgery, and vaginal rejuvenation, etc.

SUMMARY

The present disclosure relates to medical devices, and more specifically provides RF therapeutic apparatuses for vaginal tightening.

A radio-frequency apparatus is provided for vaginal tightening. The apparatus includes a main engine, a connection device, an applicator, and a negative plate, wherein the applicator includes a hand-held component and a treatment plug. The treatment plug has multiple RF electrodes distributed thereon, and has a size similar to the target tissue such that no movement is necessary during treatment.

The RF output device may include a RF electrode module with multiple sets of RF electrodes; a RF generator matches with the output of the multiple groups of RF electrode corresponding to the multiple RF sources, and the described multiple RF source, driving the circuit through multiple RF electrode correspondingly connect to multiple sets of RF electrode; Controller: Connect the RF electrode driving circuit, trigger the stated electrode driving circuit conduction at a preset frequency output RF excitation source. Driving the described multiple groups of RF electrode with multiple RF source circulating conduction to work in turn. The perfect solution for the existing problem of unevenly RF current electrode treatment distribution is to use the RF electrode driving circuit driving alone the conduction between RF electrode and RF source, at the same time by adopting multiple sets of RF electrode conduction for RF electrode configuration treatment, to ensure uniform distribution between each group of RF electrode current.

DETAILED DESCRIPTION

Figure 1:
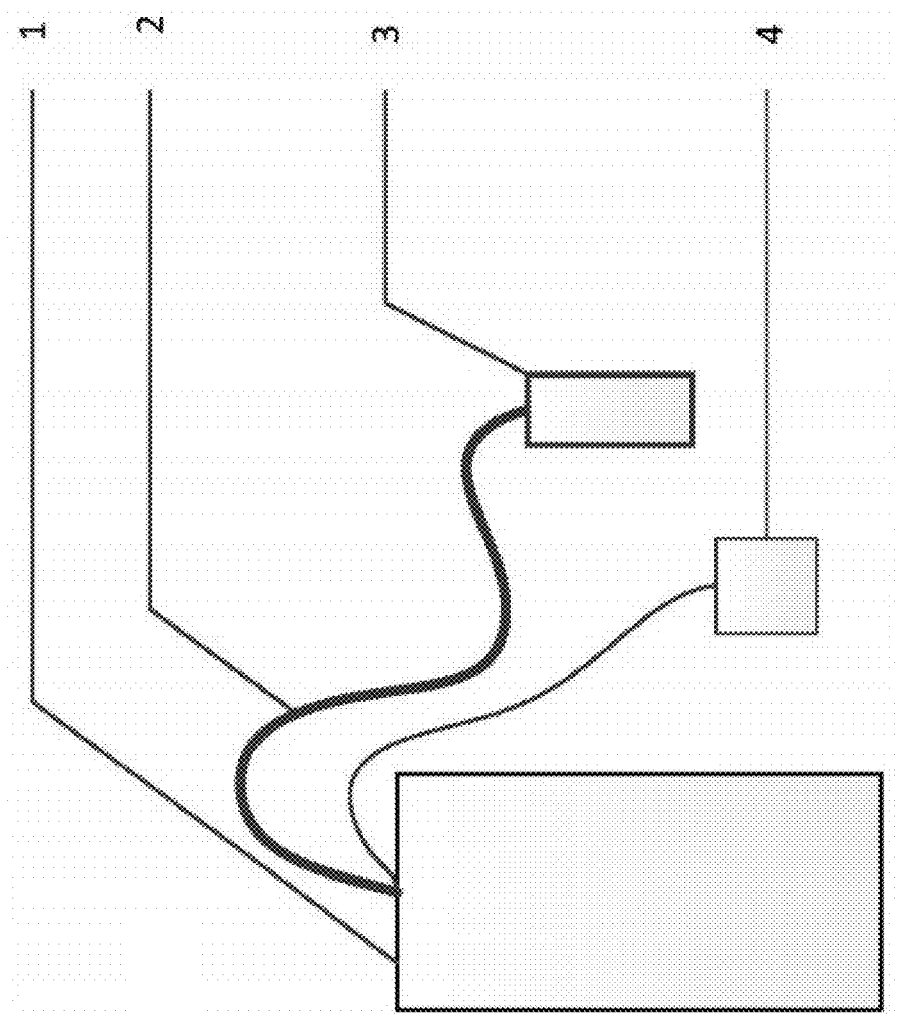
FIG. 1 is a schematic diagram of an RF therapeutic apparatus for vaginal tightening according to some implementations.

For many female patients, vaginal relaxation brings them various risks, physiological stress urinary incontinence, the reduction of vaginal self-cleaning ability, which leads to various inflammation; meanwhile unpleasant sex which will increase divorce risks etc.

Among present vaginal rejuvenation products, like V2LR by Deka, with its patent number WO 2011/096006A1, and WO 2012/037954A1 by FOTONA, the treatment on vaginal wall by applicator is based on plane mirror which can only guarantee vertical irradiation on few areas with other areas in oblique incidence, resulting in inadequate penetration depth and ineffective therapy. The treatment process and operation is complex because target tissue is in circular, as a consequence, the applicator is required to rotate during treatment. Laser fractional treatment will cause micropores on vagina mucosa, resulting in damages on mucosal tissue and infection risks; as high cost of laser components the treatment tool that access into vagina will be disinfect repeatedly then use, which will increasing the treatment risks.

Fractional Radio Frequency (RF) is a technology with parallel matrix on the treatment tip which can cause micro aperture on skin, RF electric current flow through the aperture to the deep skin, at the same time, it can gasify the skin, flow through the deep skin, activate collagen neogenesis and reconstruction, use a point on surface for different skin problems to achieve comprehensive improvement, solve skin ageing problems like large pore, roughness and lackluster, relaxation, appearance of fine lines, and so on.

While fractional RF technology has many benefits, in existing fractional RF equipment, it has multiple anodes and cathodes, which will cause uneven distribution of the electric current, uneven energy distribution at various points during the treatment, especially some points have higher treatment dose, or some treatment points can't meet the requirements.

The present disclosure helps solve the technical problems in present technologies, specially offers an innovative RF therapeutic device on vaginal wall tightening.

To realize aforementioned purposes, the present disclosure provides a RF therapeutic device on vaginal wall tightening which includes the main engine 1, connection device 2, applicator 3 and negative plate 4 with the characteristics that the abovementioned applicator 3 contains hand-held component and treatment plug; the abovementioned main engine is connected to hand-held component of the applicator 3 through connection device 2; size of the abovementioned treatment plug is equivalent to the length of the target tissue, therefore, it is no need to move during treatment; on the surface of the abovementioned treatment plug, multiple RF electrodes 22 are distributed with part of it are RF positive and another part are RF negative.

Beneficial effect of aforementioned technical solution: the abovementioned applicator comprises hand-held component, as well as treatment plug which is replaceable to guarantee clean and safe application. Meanwhile, end section of treatment plug is larger than all others areas, as a consequence, it provides a better treatment on vaginal orifice with effective therapeutic effect.

The abovementioned RF therapeutic device on vaginal wall tightening is optimized. The abovementioned hand-held component includes: handle 21 and cooling water circuit 24; within the abovementioned handle 21, the cooling water circuit 24 is covered which extended outside from the handle 21; the extension of the abovementioned cooling water circuit 24 from the handle 21 covers RF electrodes 22 inside.

Beneficial effect of aforementioned technical solution: the abovementioned cooling water circuit is used to cool the device down to make user comfortable.

The abovementioned RF therapeutic device on vaginal wall tightening is optimized. The abovementioned treatment plug includes thermal conductive elements 23 and temperature sensor 26.

Inside of the abovementioned treatment plug, RF electrodes 22 are contained; thermal conductive element 23 is contained in inner side of the abovementioned RF electrodes 22; inner side of the abovementioned thermal conductive element 23 has the cooling water circuit 24 extended from handle 23; the abovementioned temperature sensor 26 is arranged within the RF electrodes 23.

Beneficial effect of aforementioned technical solution: the abovementioned thermal conductive element 23 and temperature sensor 26 are able to supervise changes of the user body and carry out physiotherapy through thermal conductive element.

The abovementioned RF therapeutic device on vaginal wall tightening is optimized. The abovementioned temperature sensor 16 includes three kinds of configurations inserted into RF electrodes 22, attached on the upper surface of RF electrodes 22 and attached on the lower surface of RF electrodes 22, with thermal isolated from the heat conductive elements 23; quantity of the abovementioned temperature sensor 26≥1.

Beneficial effect of aforementioned technical solution: three kinds of configurations are able to provide a better therapeutic effect.

The abovementioned RF therapeutic device on vaginal wall tightening is optimized. The abovementioned treatment plug includes identification chip 25 which is placed within the treatment plug.

Beneficial effect of aforementioned technical solution: the abovementioned identification chip is able to identify whether the treatment plug is used or not, and in reutilization or not, avoiding healthy and safety risks because of reuse.

Additionally, identification chip also has double signal transmission interfaces respectively for RF signal and temperature sensor signal.

The abovementioned RF therapeutic device on vaginal wall tightening is optimized. Size of the abovementioned treatment plug is with diameter 2.5 cm-3.75 cm and longitudinal length 7 cm-15 cm. Beneficial effect of aforementioned technical solution is that the optimized diameter and longitudinal length are applicable for the optimized size selected by most of the users.

The abovementioned RF therapeutic device on vaginal wall tightening is optimized. These abovementioned RF electrodes are one of the shapes of round, bar, linear, ring, polygon and irregular arcs or random combinations. The electrodes account for 5%-80% of the outer wall area of the whole treatment plug.

Beneficial effect of aforementioned technical solution is that outer wall areas of the whole plug is optimized.

The abovementioned RF therapeutic device on vaginal wall tightening is optimized. Outline shape of the abovementioned RF electrodes adopt rectangular RF electrodes in small plate like, regular/irregular arranged on the whole outside surface of the hand piece.

Beneficial effect of aforementioned technical solution: because the RF electrode has effect on target tissue. They are arranged in accordance with different skin areas to ensure treatment stability.

The abovementioned RF therapeutic device on vaginal wall tightening is optimized. Outline shape of the abovementioned RF electrodes adopts bar RF electrodes distributed on outside of plug.

Beneficial effect of aforementioned technical solution: because the RF electrode has effect on target tissue. They are arranged in accordance with different target skin areas to ensure treatment stability.

The abovementioned RF therapeutic device on vaginal wall tightening is optimized. The abovementioned RF electrodes are in circular.

Beneficial effect of aforementioned technical solution: because the RF electrode has effect on target tissue. They are arranged in accordance with different target skin areas to ensure treatment stability.

The abovementioned RF therapeutic device on vaginal wall tightening is optimized. The abovementioned RF electrodes are in circular with certain inclination or in vertical angle.

Beneficial effect of aforementioned technical solution: because the RF electrode has effect on target tissue. They are arranged in accordance with different target skin areas to ensure treatment stability.

The abovementioned RF therapeutic device on vaginal wall tightening is optimized. The abovementioned RF electrodes are arranged in linear unipolar and/or in bipolar, forming current loop within a local small area.

Beneficial effect of aforementioned technical solution: because the RF electrode has effect on target tissue. They are arranged in accordance with different target skin areas to ensure treatment stability.

The abovementioned RF therapeutic device on vaginal wall tightening is optimized. The abovementioned RF electrodes are arranged in linear unipolar and/or in bipolar. One of the poles is located inside and another pole is located outside; or RF electrodes are arranged in fractional bipolar RF style with both polar cross distributed. RF Polar difference shall no more than twice.

In summary, because of application of above technical solution, beneficial effect of various embodiments disclosed herein may include one or more of: cost of the RF therapeutic device on vaginal wall tightening is largely decreased, with safety increased and therapeutic effect improved.

The present disclosure, aiming on at least solve the technical problems in present technologies, more specially provides an innovative RF therapeutic device on vaginal wall tightening.

To achieve abovementioned purposes of the present disclosure, it offers a RF therapeutic device for vaginal orifice tightening which includes the main engine 1, connection device 2, applicator 3 and negative plate 4, with the key point that the abovementioned applicator 3 contains handheld component and treatment plug; the abovementioned main engine is connected to hand-held component 101 of the applicator 3 through connection device 2; the cross section of the abovementioned treatment plug end part is bigger than the rest part of treatment plug, multiple radio-frequency electrodes are distributed on the end part of treatment plug, some of them are RF anode, some are RF cathode, or all are RF anode.

Beneficial effect of aforementioned technical solution: treatment handpiece comprises handle part and treatment plug, as to treatment plug, it can be changed and replaced, to ensure user safety and health. Meanwhile, the end cross section of treatment plug is larger than all the left parts, as a consequence, it provides a better treatment on vaginal orifice with effective therapeutic effect.

The described RF treatment device for vaginal orifice tightening is optimized, The abovementioned RF electrodes is one of the shapes of round, bar, linear, ring, polygon and irregular arcs or random combinations.

Beneficial effect of aforementioned technical solution: RF electrodes target on the treatment areas, we can set different electrode array according to different patients targeted skin, to guarantee treatment stability.

The described RF treatment device for vaginal orifice tightening is optimized, he abovementioned RF electrodes are bar shape unipolar RF electrodes or linear RF electrodes.

Beneficial effect of aforementioned technical solution: RF electrodes target on the treatment areas, different electrode arrays can be set according to different patients targeted skin, to guarantee treatment stability.

The described RF treatment device for vaginal orifice tightening is optimized. RF electrodes are bar shape bipolar electrodes, linear bipolar RF electrodes, or linear bipolar RF electrodes with one pole linear shape, another pole surrounded by bar shape electrodes.

Beneficial effect of aforementioned technical solution: RF electrodes target on the treatment areas, we can set different electrode array according to different patients targeted skin, to guarantee treatment stability.

The described RF treatment device for vaginal orifice tightening is optimized. RF electrodes are fractional unipolar RF electrodes.

Beneficial effect of aforementioned technical solution: RF electrodes target on the treatment areas, we can set different electrode array according to different patients targeted skin, to guarantee treatment stability.

The described RF treatment device for vaginal orifice tightening, the optimized RF electrodes are fractional shaped bipolar RF electrodes or fractional shape bipolar RF electrodes with one pole fractional shape, another pole surrounded by bar shape electrodes, or fractional shaped RF electrodes, RF anodes and cathodes are interval distributed.

Beneficial effect of aforementioned technical solution: RF electrodes target on the treatment areas, we can set different electrode array according to different patients targeted skin, to guarantee treatment stability.

The described RF treatment device for vaginal orifice tightening is optimized. Including handheld part 101 and treatment plugs are fixed by card slot.

Beneficial effect of aforementioned technical solution: handheld part 101 and treatment plugs are fixed by card slot, setting based on user habits, so that can be easily installed and removed.

The described RF treatment device for vaginal orifice tightening is optimized. Including treatment hand piece 3 comprises knob and plug, be connected by lathe thread.

Beneficial effect of aforementioned technical solution: handheld part and treatment plugs are fixed by card slot, setting based on user habits, so that can be easily installed and removed.

The described RF treatment device for vaginal orifice tightening is optimized. The grip part of treatment handpiece 3 including handle part 101, identification chip and the RF signal source interface male end 107, cooling water pipe 102 part, handle part 101 is setting according to the shape like hand, handle part top 101 connect to identification chip and the RF signal source interface male end 107, identification chip and the RF signal source interface female end 106 connect to identification chip male end 107, one end of cooling water pipe 102 connect to handheld part top 101, another end connect to thermal conductive element 105.

Beneficial effects of the aforementioned technical solution may include: the described identification chip can ensure the treatment plug is disposable, not secondary use, cooling targeted tissue by cooling water pipe.

According to some embodiments, the abovementioned RF treatment device is configured for vaginal orifice tightening, the abovementioned treatment plug including thermal conductive element 105, cooling device and at least one temperature sensor 104 fix on forepart of the RF electrode 103, or embed in RF electrode 103, or fix on rear end of RF electrode 103 and thermally isolated from thermal conductive element 105.

Beneficial effects of aforementioned technical solution may include: the described temperature sensor monitor temperature in real time, ensure the user can adapt to the treatment temperature.

In summary, because of application of above technical solution, beneficial effect of this disclosure are:

Cost of the RF therapeutic device on vaginal wall tightening is largely decreased, with safety increased and therapeutic effect improved.

In some implementations, an RF output device is provided to solve the uneven distribution of current problems during the treatment caused by multiple anodes and cathodes of the existing frictional RF device.

To achieve the above purposes and other related purposes, various technical solutions are provided as follows.

A RF output device, including: RF electrode module with multiple sets of RF electrodes; RF generator for output and described more groups of RF electrode corresponding to the number of multiple RF source, and the abovementioned RF output source connect to multiple sets of RF electrodes through corresponding number of RF electrode; Controller, connect the RF driving circuit to trigger the RF electrode driving circuit conduction according to the preset excitation frequency output, to driving the abovementioned multiple groups of RF electrode with multiple RF source circulating breakover to work in turn.

The RF electrode driving circuit in abovementioned RF output device is optimized, including: optical coupler, transistor and relay, the abovementioned transistor connect the optical coupler through the first resistance, the transistor collector electrode connect to the relay, the emitting electrode of transistor connect to the output source.

As a further improvement of the optimized solution of RF electrode treatment device, the abovementioned optical coupler connects to one end of the second resistors by its input terminal, another end of the second resistors connect to the controller, optical coupler connect to ground by its another input terminal, optical coupler connect to power source by one of its output terminal, optical coupler connect to another terminal of the first resistors by its another output terminal, another terminal of the first resistors connects to the base electrode of transistor, the collector electrode of the transistor connect to the upper end of the coil on relay, the another upper end of the coil on relay connects to the power source, the switch on relay is normally open SW-DPST, connect to one group of RF electrode and RF source respectively, the abovementioned transistor emitting electrode connect to the ground.

As mentioned above, this disclosure of the RF output device have following beneficial effects: to drive alone the RF electrode and the RF breakover source of RF electrode driving circuit, ensure uniform current distribution between each group of RF electrodes, this is a very good solution for RF current distribution unevenly in the existing electrode treatment.

Implementation case will be described in following. Example of the abovementioned implementation case show in attached Figures, in which identical or similar symbols indicate identical or similar elements or elements with identical or similar functions. The reference Figure described implementation cases are only examples, and is only used to explain this disclosure and cannot be used as limitation on this disclosure.

The terms used in the description, such as "longitudinal," "transversal," "up," "down," "front," "behind," "left," "right," "vertical," "horizontal," "top," "bottom," "inside" and "outside" etc, are based on directions the Figures indicated, and for disclosure description and description simplification only, rather than indicate or imply the device and elements are required to have specified directions, or structured and operate in a specified direction. Therefore, it can't be taken as limitation on this disclosure.

Otherwise specified and limited, terms used in this disclosure description, such as "installation," "connected" and "connection" are with a broad meaning For example, it could be mechanical or electrical connection, or two inner elements connection; it could be direct correction or connected by a media. For normal technicians in this field, they are allowed to acquire the exact meaning of above terms based on actual conditions.

Various embodiments provide a radio-frequency device on vaginal wall tightening, including treatment main engine 1 and applicator 4.

The abovementioned treatment plug can comprise a hand piece and plug. The plug can comprise functional units, such as RF electrode, thermal conductive elements, temperature sensor and RF identification module etc.

The horizontal section of the abovementioned plug can be in circular or similar circular with diameter 2.5 cm-3.75 cm; longitudinal length can be in the range of 7 cm-15 cm.

The abovementioned temperature sensor can be equipped with 1-6 temperature sensors used to monitor temperature on skin.

Integral arrangement of the abovementioned RF electrode could be plate like rectangular RF electrode, or bar like electrode, or circular RF electrode, or circular RF electrode in angle of inclination.

The abovementioned RF electrode on the treatment plug is a electrode matrix which comprises multiple RF electrode units.

The abovementioned RF electrode unit could be unipolar or bipolar.

The abovementioned unipolar RF electrode unit could be in plate or in linear or fractional unipolar RF electrode.

The abovementioned bipolar RF electrode unit could be in linear or fractional.

Various embodiments are related to a RF therapeutic device on vaginal wall tightening which is able to simplify treatment procedure and reduce possibility of unremarkable curative effect, as well as clinic risk reduction.

Technical solution of various embodiments can be as follow: it includes main engine 1, connection device 2 and treatment hand piece 3. The main engine 1 connect with treatment hand piece 3 through connection device 2 which comprises cooling water circuit pipe, RF power cord, signal connecting line of temperature sensor and connecting line of identification chip. The treatment hand piece 3 comprises hand-held components and disposable plug, in which hand-held components comprises handle 21 and cooling water pipe 24; the disposable plug comprises RF electrode 22, thermal conductive element 23, identification chip 25 and temperature sensor 26.

RF power inside of the main engine is continuous which provide long time heating on target tissue to stimulate collagen regeneration, such as heat target tissue for 4-10 s under 55-70° C. to heat collagen and cause its degeneration.

Applicator hand-held components mainly provide cooling source, thermal conductive unit and connecting cord.

Applicator has cooling device. Flow direction of current will form loop among RF positive pole, vagina mucosa, subcutaneous tissue and RF negative pole. Impedance of mucosa tissue will cause heating, in order to protect it from injury, 16-28° C. cooling temperature is required for cooling device.

Cooling system inside of treatment handpiece comprises cooling source and thermal conductive elements. The cooling source could be circulating cooling, semi-conductive cooling and cold spray cooling. Thermal conductive elements adopt material with high thermal conductivity, such as aluminum, red copper etc.

Disposable plug is equipped with three main functional elements: RF electrode 22, temperature sensor 26 and identification chip 25.

Plug-in treatment applicator is in ergonomic design. Its handle is cylindrical or similar cylindrical, and the horizontal section is in circular or similar circular which can reduce fiction when inserting into vagina, avoiding physical trauma on human body.

Flexible circuit plate and curvature processing of hard electrode material are both applicable for RF electrode.

RF electrode has various shapes, such as in circular, bar, plate. Negative plate attachment on hand piece electrode in different shapes is diverse.

The heating mechanism of RF on skin. Energy received by the target is $Q=I^2Rt$, in which I is current passing through tissues, R is impedance of tissue through current areas, and t is time of continuous current. Skin temperature increasing is $\Delta T=Q/(C \cdot M)$, in which C is coefficient of thermal of tissue $J/(kg.° C.)$, M is weight of heated tissue areas (kg).

Inside the skin, there is current flowing among electrodes, in which most of electrical charge will move by connecting. The detail shows that the nearest distance and the smallest impedance.

Tissue impedance R in treatment areas is in intrinsic property, controlling energy each second on the target and relying on change on current density I. Because C is the intrinsic property of tissue, M is weight of skin around electrodes. Skin temperature rising is related with energy Q received on the target. Amount of current density is affected by sizes and distances among electrodes.

Treatment applicator can use bipolar RF, unipolar RF and combination of unipolar and bipolar. Unipolar RF has features of deep penetration and scattered energy. Bipolar RF has features of focused energy and shallow penetration.

Figure 3:
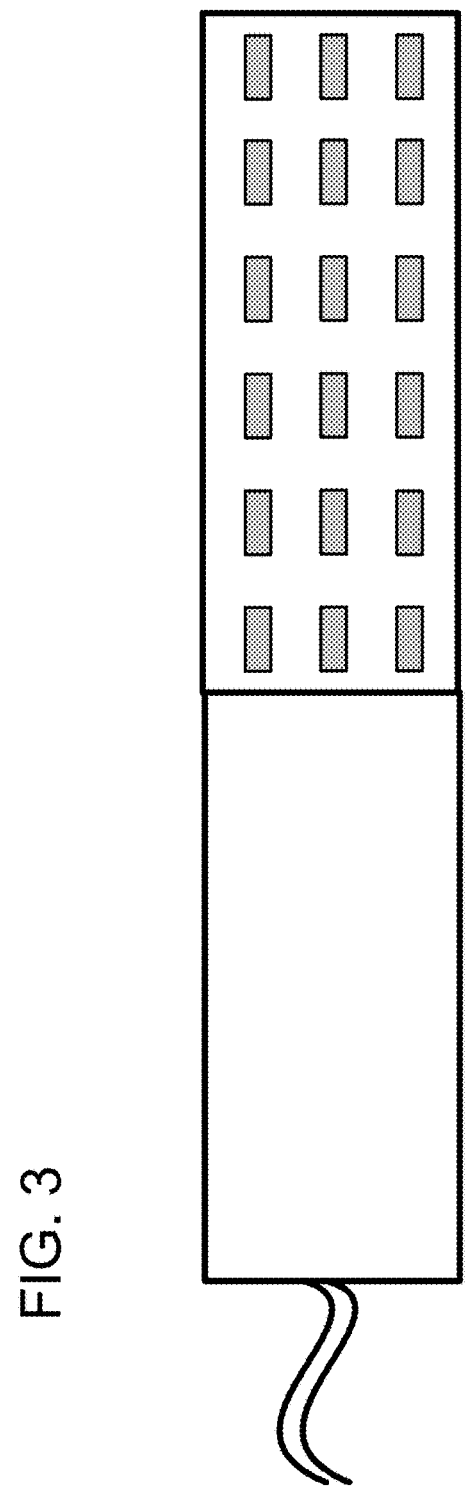
FIG. 3 is a schematic diagram of a flat-shaped electrode hand piece of the RF therapeutic apparatus according to some embodiments.

Flat like RF electrode in FIG. 3 is controlled by single unipolar. During the treatment, it is able to ensure energy on vaginal wall is the same. The front-end RF electrode between negative plate, end electrode between negative plate forms loop. These two areas are close to positive, and current density I is the same, and energy Q received on this area is the same.

Figure 4:
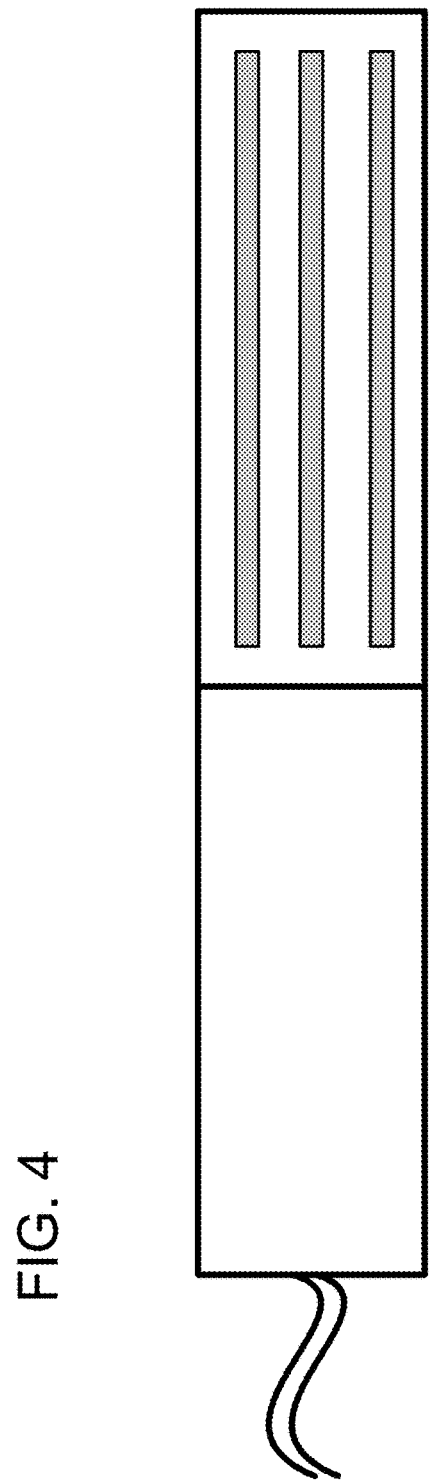
FIG. 4 is a schematic diagram of a bar-shaped electrode hand piece of the RF therapeutic apparatus according to some embodiments.

Amount of bar like RF electrode in FIG. 4 is less than that in FIG. 3. Negative plates have to be attached on the body during treatment, and it will cause the distance from the same electrode to negative plate are different, resulting current density difference in treatment areas of the same electrodes, and target temperature rising difference. Cooling function in applicator keeps skin temperature rising within control range. Meanwhile, electrode area is increased and treatment speed is accelerated.

Figure 5:
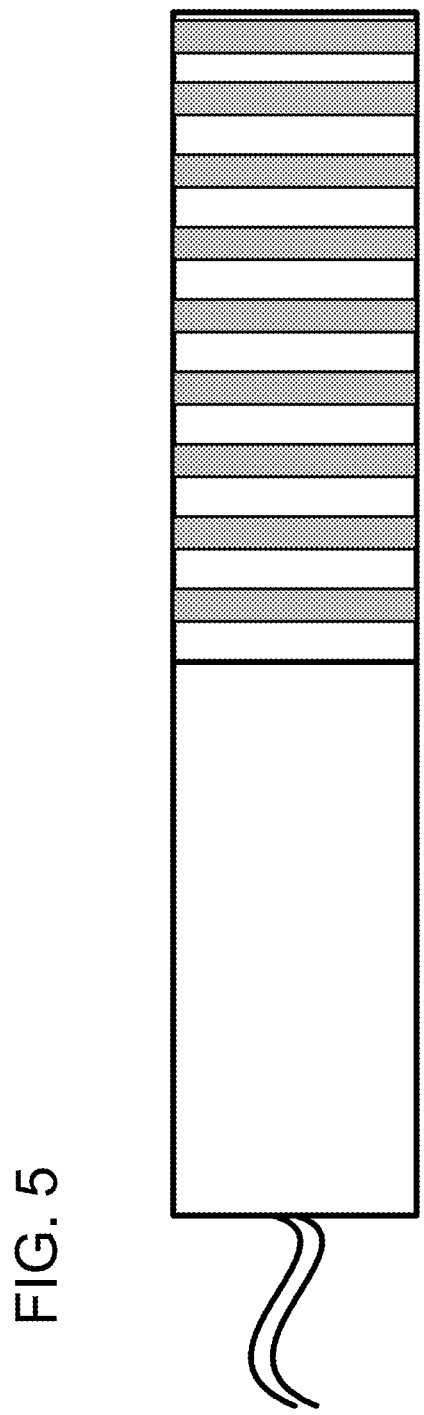
FIG. 5 is a schematic diagram of a circular electrode hand piece of the RF therapeutic apparatus according to some embodiments.
Figure 6:
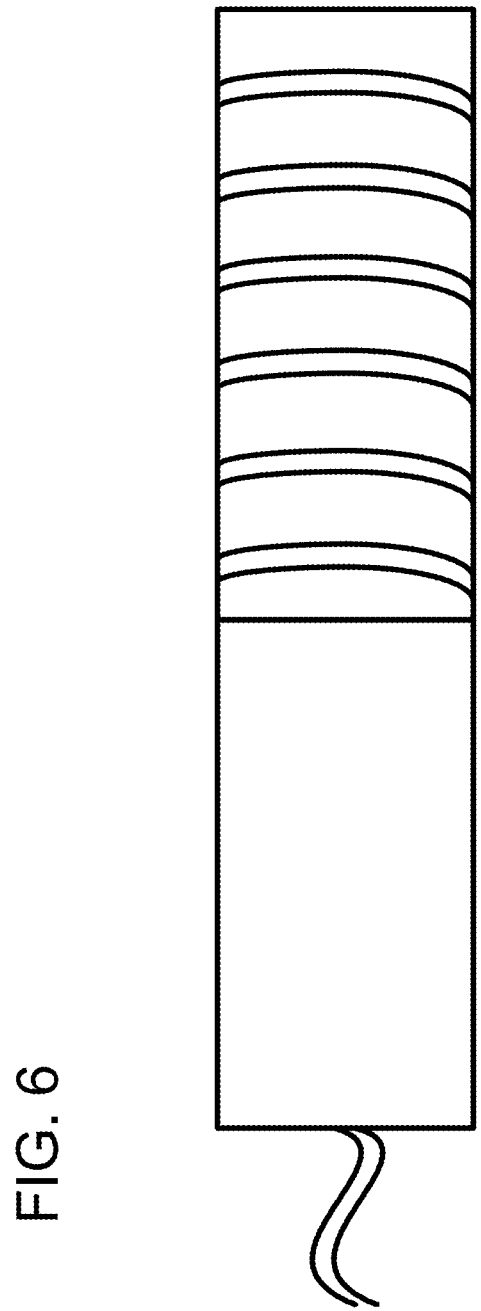
FIG. 6 is a schematic diagram of an oblique ring-shaped electrode hand piece of the RF therapeutic apparatus according to some embodiments.

Amount of circular like RF electrode in FIGS. 5 and 6 is less than that in FIG. 3 which will improve therapeutic effect. The advantage is that when in bipolar, circuit is formed between two RF electrodes. The same electrodes are equipotential, and the distance to the other polar is the same, and delivery path in human tissue is the same, so the therapeutic effect of each area can be guaranteed. It is useful to avoid uneven heating under mono- and bipolar arrange. Because of difference of circular wall length, it will result different impedance.

In FIG. 6, it is inclined circular RF electrodes which used to adjust angle between applicator and negative plate to ensure distance from the different areas on the one RF electrode to negative plate is the same, and guarantee even treatment effect. This kind of electrode arrangement has a higher evenness for both unipolar and bipolar.

Treatment applicator can use bipolar RF, unipolar RF and combination of unipolar and bipolar. Unipolar RF has features of deep penetration and scattered energy. Bipolar RF has features of focused energy and shallow penetration.

Adopt small RF electrodes to ensure even energy distribution on vaginal wall. For example, separate the applicator into 10-200 RF electrodes. Electrodes are able to surround the linear electrode with the dimensions 0.5 mm×100 mm, or rectangular electrode with the dimensions 5 mm×10 mm or 10 mm×10 mm. RF electrode account for part of the applicator inserted into vagina 10%-100%.

Meanwhile, to ensure a better contact of RF electrode with vaginal wall, applicator diameter is set as 2.5 mm-3.5 mm. Length of electrodes inside of vagina is 7 cm-15 cm.

RF current flows through the path with the lowest impedance, and distance between vaginal applicator is 3 cm in up and down and 10 cm in front and back, obvious impedance is exist on different points of applicator of large electrode, resulting part of contact areas receive high amount of dosages, and other area far away from negative plate are under treatment.

Temperature sensor contact with skin on applicator could be single or multiple, which used to supervise skin temperature. The temperature sensor includes three kinds of configurations: inserted into RF electrodes, attached on the upper surface of RF electrodes and attached on the lower surface of RF electrodes, with thermal isolated from the heat conductive elements.

Cooling system is working before treatment. The cooling system will operate for 10-60 s. System judge the contact of electrode with skin based on received skin temperature from temperature sensor. For example, the cooling temperature set at 20° C., and start the system to observe skin temperature is approaching cooling water temperature or not, and distinguish good contact of electrode with skin. After starting of cooling system, cooling temperature of temperature sensors will be supervised. The cooling system is considered as in normal condition on the condition that temperature checked by different temperature sensors is the same or with difference ±1° C., and in a good contact with skin.

Vagina requires clean and safe treatment, therefore, the disposable plug is adopted to avoid cress infection caused poor sterilization and improve safety and reliability. Meanwhile, the disposable is equipped with identification chip which can avoid repeated application of sterilized components. After starting, the system can check application condition of the plug connected. For example, it is possible to set that the consumables is not allowed to continue to work after 2 hrs connection with the system, or the consumables is allowed to connect with the system for only once etc. The system will be prohibited to operate once beyond the restrictions.

As shown in FIG. 1, the system comprises the main engine 1, connection device 2, treatment applicator 3 and negative plate 4.

RF power, cooling device and screen are equipped within the main engine 1 with RF power is continuous. Top of the abovementioned main engine 1 is connected with end of treatment applicator 3 through connection device 2. The treatment applicator 3 comprises handle and treatment plug.

Figure 2:
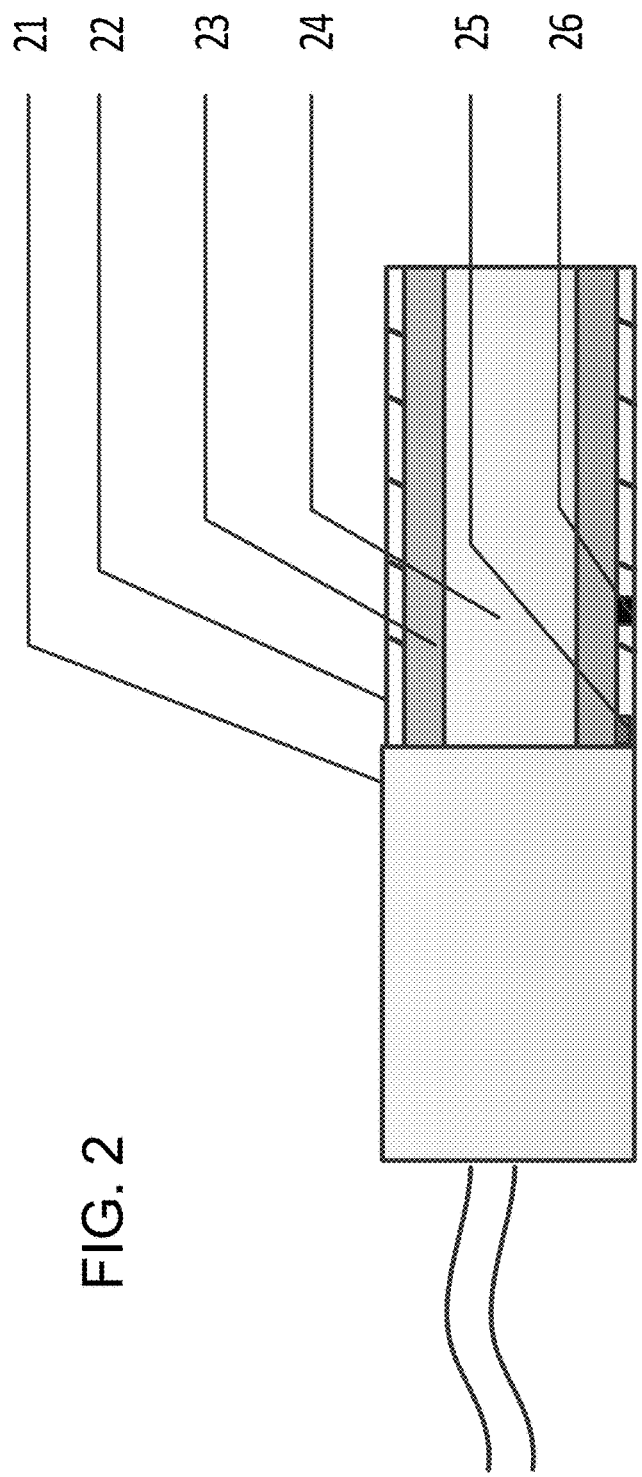
FIG. 2 is a schematic diagram of a hand piece of the RF therapeutic apparatus according to some embodiments.

FIG. 2 shows structure of treatment applicator which comprises handle and disposal treatment plug. The disposal plug is stuck in the treatment plug. Handle comprises handle 21 and cooling circuit 24; the disposal plug comprises RF electrode 22, thermal conductive element 23, the identification chip 25 and temperature sensor 26. Outline section of the treatment plug is in circular or similar circular with outer dimension 2.5-3.75 cm; longitude length 7 cm-15 cm, and front and back in cylindrical.

FIGS. 3-6 illustrate the integral arrangement sketch of RF electrode.

As shown in FIG. 3, plate like rectangular RF electrodes are covered on the outer surface of the applicator. It could be in regular or irregular distribution.

As shown in FIG. 4, bar like rectangular RF electrodes are covered on the outer surface of the treatment plug.

As shown in FIG. 5, circular rectangular RF electrodes are covered on the treatment plug.

As shown in FIG. 6, the circular RF electrode is in inclination because after inserting, the applicator has a angle with the lying body, and inclined circular RF electrode is more evenly distributed.

Figure 7:
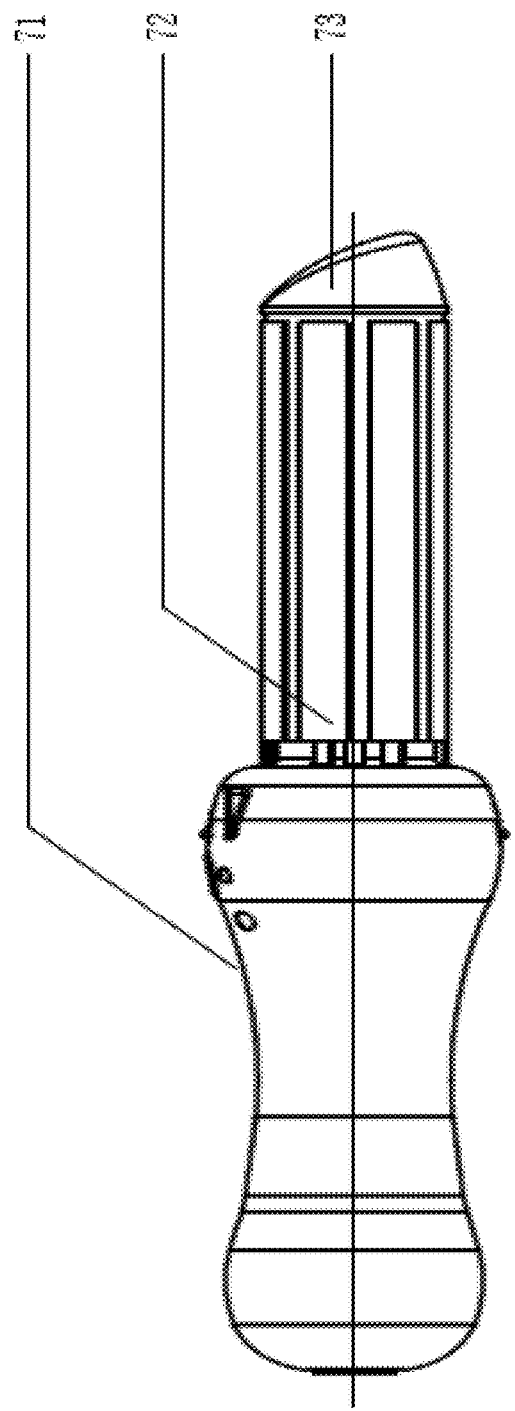
FIG. 7 is a schematic diagram of an RF applicator piece of the RF therapeutic apparatus according to some embodiments.

FIG. 7 shows treatment plug sketch. 71 is handle, 72 is RF electrode, front end of treatment plug 73 is in taper with curvature, and no RF electrode is distributed on this area, in order to decrease applicator friction inside the vagina. Front end of treatment plug 23 is tapering with curvature.

Figure 8:
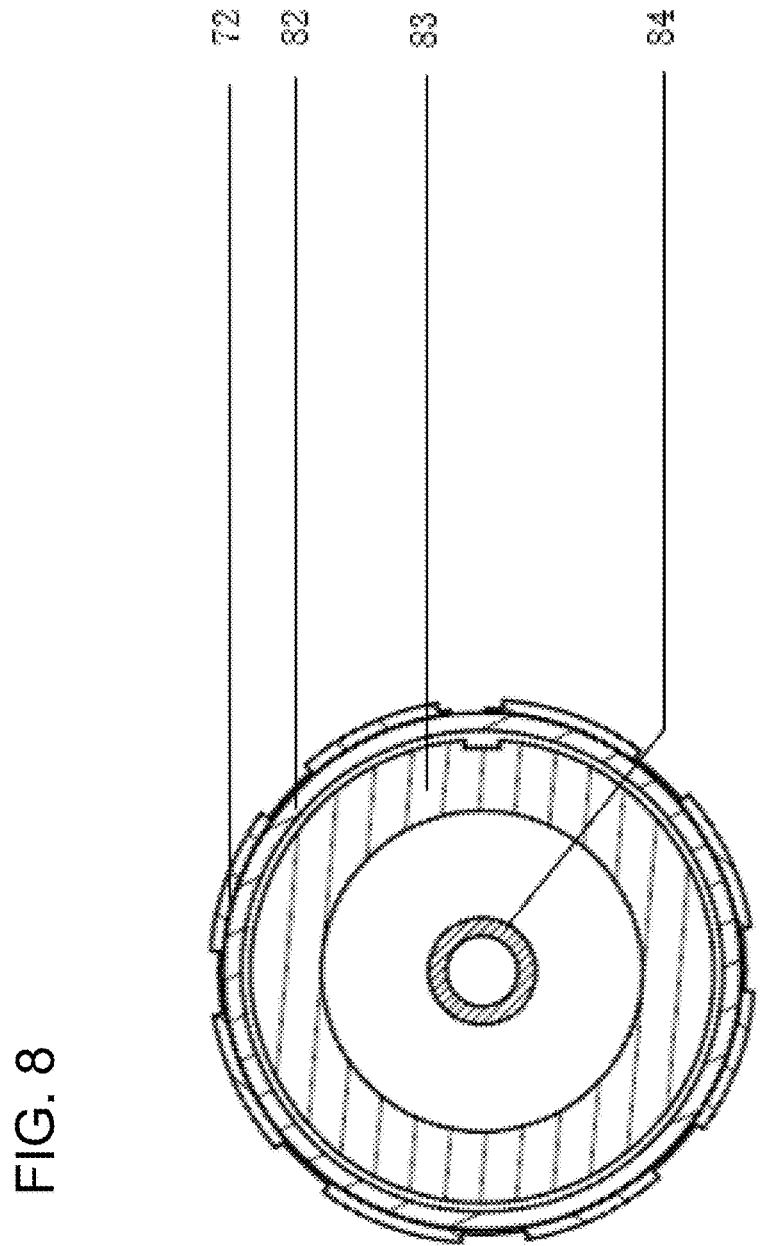
FIG. 8 is a transverse sectional view of the RF applicator of the RF therapeutic apparatus according to some embodiments.

FIG. 8 shows the section sketch of treatment plug inserted into vagina. RF electrodes 72 carry out treatment by touching with vaginal wall. The abovementioned RF electrode 72 is evenly distributed on thermal conductive element 82. Cooling circuit is covered inside of the abovementioned thermal conductive element 82 to delivery heat and cooling mucosal tissue. The abovementioned cooling waterway is concentric path with a dual water cycle which comprises cooling water Outer wall 83 and isolation tube 84. The isolation tube wall of water inlet and circuit waterway, 83 is outer wall of cooling waterway which is next to thermal conductive element. The cooling waterway isolation tube wall 84 has clearance with top of cooling waterway 24 to ensure cycling waterway of cooling waterway outer wall is able to flow in from cooling waterway isolation tube wall and return to handle 72 of RF device.

Figure 9:
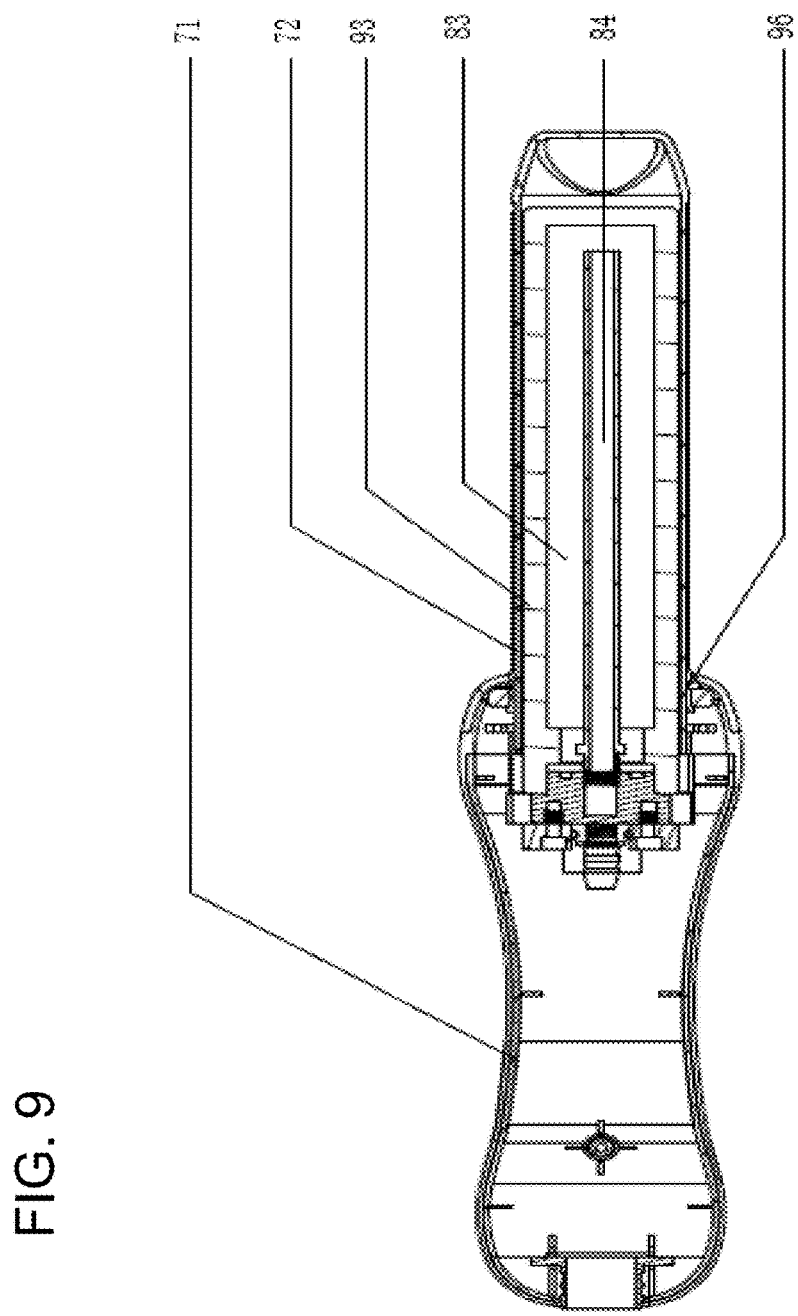
FIG. 9 is a longitudinal sectional view of the RF applicator of the RF therapeutic apparatus according to some embodiments.

FIG. 9 shows section sketch of treatment applicator. Numeral reference 71 refers to a handle, 72 is RF electrode, 93 is thermal conduct component, 83 is outer wall of cooling waterway, 84 is isolation tube wall of cooling waterway, and 96 is identification chip. Insert the end part of treatment plug into handle 71, and stuck it in the slot, which means inside toward groove on extension of end of treatment plug is match with embossment on handle 71, to avoid shaking Identification chip 96 is inserted into the end part of the plug. When it is in repeated application, identification chip 96 will tip user. The chip is well-known in medical device field, so no need to describe.

FIG. 12-FIG. 19 are detailed shape sketches of the RF electrode.

Figure 12:
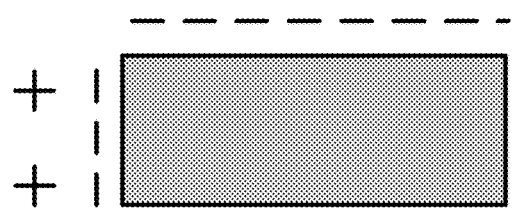
FIG. 12 is RF electrodes section views of RF treatment device.

As shown in FIG. 12, single RF electrode could be in plate like, rectangular, and circular, and it could be used in various RF electrodes shown in FIGS. 3-6.

Figure 14:
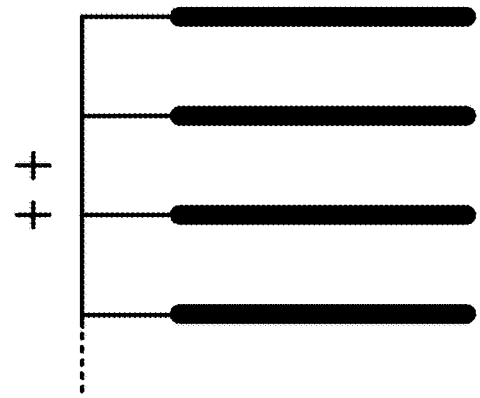
FIG. 14 is the bar shape electrode (unipolar RF) schematic diagram of RF treatment device for vaginal tightening.

As shown in FIG. 14, single RF electrode is in linear and unipolar.

Figure 15:
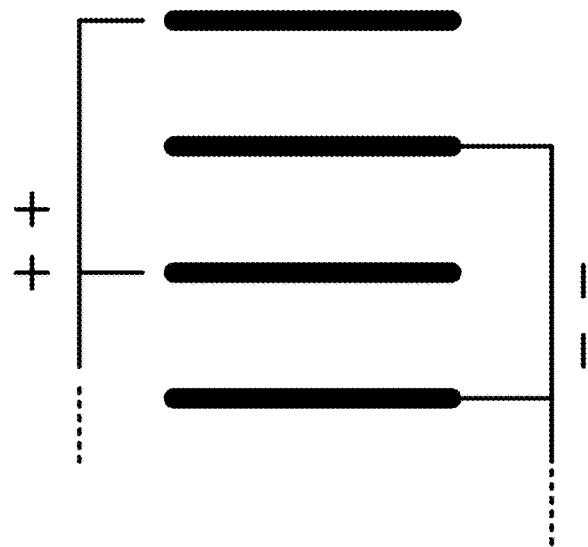
FIG. 15 is the bar shape electrode(bipolar RF) schematic diagram of RF treatment device for vaginal tightening.

As shown in FIG. 15, single RF electrode is in linear, forming current circuit inside of a local small area.

Figure 16:
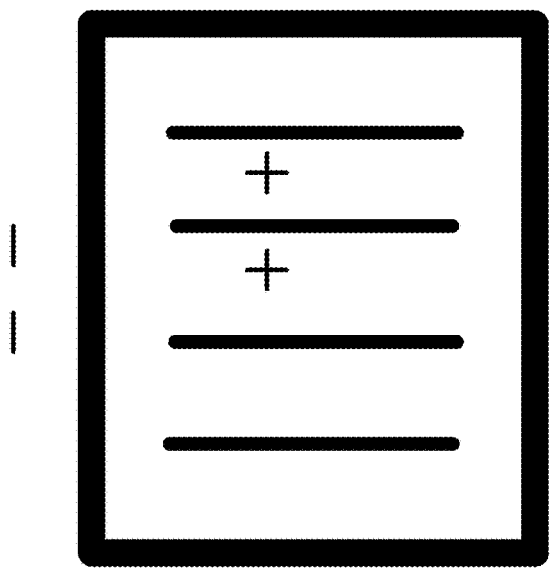
FIG. 16 is the bar shape electrode(bipolar RF) schematic diagram of RF treatment device for vaginal tightening.

As shown in FIG. 16, single RF electrode is in linear and bipolar. Inside is one polar of the RF and outside is another polar of it. Area difference between positive and negative polar of RF shall not exceed twice.

Figure 17:
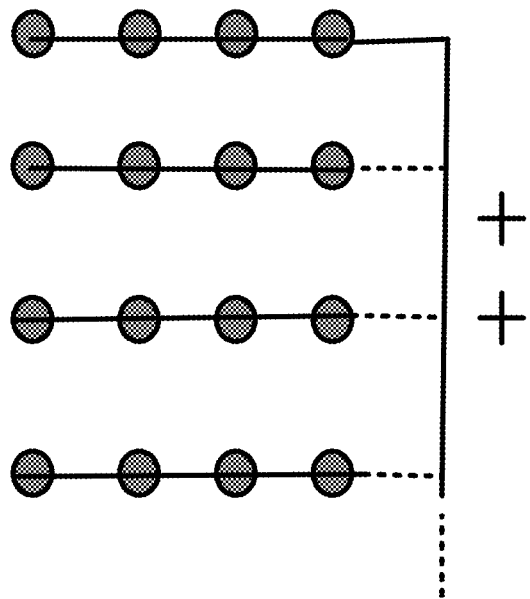
FIG. 17 is the fractional unipolar RF electrodes schematic diagram of RF treatment device for vaginal tightening.

As shown in FIG. 17, single RF electrode is fractional unipolar.

Figure 18:
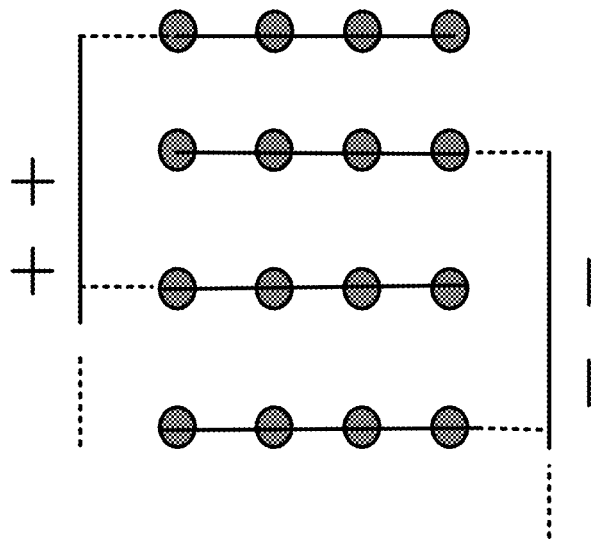
FIG. 18 is the fractional bipolar RF electrodes schematic diagram of RF treatment device for vaginal tightening.

As shown in FIG. 18, single RF electrode is fractional bipolar. Two polar of the RF are cross arranged. The difference of RF amount shall not exceed twice.

Figure 19:
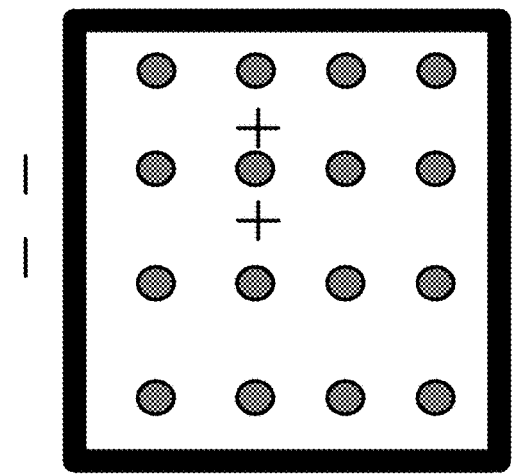
FIG. 19 is the fractional bipolar RF electrodes schematic diagram of RF treatment device for vaginal tightening.

As shown in FIG. 19, single RF electrode is fractional bipolar. Inside is one polar of the RF and outside is another polar of it.

The operation of some embodiments may include: Connect treatment applicator(negative plate, foot switch, disposal treatment plug, start, dosage setting and cut-off temperature), and run validation procedures (respective validation of applicator, negative plate, foot switch to the main engine, connection validation between treatment plug ad applicator, authorization validation of treatment plug). Insert plug into vagina to for contacting validation and skin cooling validation. After validation, the treatment process will be started.

Specific Implementation Methods (Vaginal Orifice)

Implementation case will be described in following. Example of the abovementioned implementation case show in attached Figures, in which identical or similar symbols indicate identical or similar elements or elements with identical or similar functions. The reference Figure described implementation cases are only examples, and is only used to explain this disclosure and can't be used as limitation on this disclosure.

The terms used in this disclosure description, such as "longitudinal," "transversal," "up," "down," "front," "behind," "left," "right," "vertical," "horizontal," "top," "bottom," "inside and "outside" etc, are based on directions the Figures indicated, and for disclosure description and description simplification only, rather than indicate or imply the device and elements are required to have specified directions, or structured and operate in a specified direction. Therefore, it can't be taken as limitation on this disclosure.

Otherwise specified and limited, terms used in this disclosure description, such as "installation," "connected" and "connection" are with a broad meaning For example, it could be mechanical or electrical connection, or two inner elements connection; it could be direct correction or connected by a media. For normal technicians in this field, they are allowed to acquire the exact meaning of above terms based on actual conditions.

Some embodiments disclosed herein provide a radiofrequency device on vaginal orifice tightening, which can comprise a hand piece and a disposable plug.

The disposable plug is comprising of RF electrode, thermal conductive element and fixed shell.

The abovementioned disposable plug contains selected RF identification chip and temperature sensor.

The abovementioned surface longitudinal length of RF electrode is 1-2.5 cm, transverse width is 0.5-3 cm, which forms a plane or curved surface with skin surface.

The abovementioned RF electrodes are unipolar linear shape, or bipolar linear shape, or fractional unipolar electrodes, or fractional bipolar electrodes.

The abovementioned Linear unipolar RF electrode is the entire treatment electrode comprises 1 or more than 1 RF electrodes.

One end of the abovementioned linear shaped bipolar RF electrode has a linear shape.

One end of the abovementioned fractional unipolar RF electrode is fractional shape, another end is fractional shape or linear shape.

One end of the abovementioned fractional bipolar RF electrode is fractional shape, another end is fractional shape or linear shape.

Some embodiments provide a new vagina rejuvenation treatment equipment, used to rejuvenate vagina, which can easily resolve laxity of vaginal orifice.

Technical solution of this disclosure is as follows: RF device for vagina rejuvenation, including body 1, connecting device 2 and treatment handpiece 3. The main engine 1 connect with treatment hand piece 3 through connection device 2 that comprises a cooling water circuit pipe, RF power cord, signal connecting line of temperature sensor and connecting line of identification chip; The treatment hand piece 3 comprises a hand-held components and disposable plug The operation method of this device can be as follows: get ready for the electrical device, install disposable plug on the treatment hand piece, start cooling system for 1-2 minutes, then put the applicator electrode on vaginal orifice tightly. Check the cooling system, make sure the treatment safety, set treatment dose, then deliver RF, treat the treatment, after finishing the small zone treatment, moving to the next zone along inner wall of the vagina, please note do not treat the urethra area.

Treatment hand piece comprises handle part and disposable plug, hold the treatment hand piece moving to treat. Disposable plug contains three main functional units-RF electrodes, temperature sensor and RF identification chip, disposable plug is consumable item.

Treatment hand piece does not need to be in contact with the patient, it is reused, offering cooling device and RF energy for disposable plug.

The applicator can have a cooling device, current will form a loop in RF anode, vaginal mucosa, subcutaneous tissue, RF cathode/ negative plate. Impedance of mucosa tissue will cause heating, in order to protect it from injury, 16-28° C. cooling temperature is required for cooling device.

Cooling system inside of treatment hand piece comprises cooling source and thermal conductive elements. The cooling source could be circulating cooling, semi-conductive cooling and cold spray cooling. Thermal conductive elements adopt material with high thermal conductivity. The requiring thermal conductivity is 30 Wm/k, better thermal conductivity such as copper, which is higher than 200 Wm/K.

Treatment hand piece use the internal water circulation system, offering 16-28° C. Metal conduit in treatment hand piece and heat-conducting medium in disposable plug form the cooling device in hand piece.

The treatment plug have inside temperature sensor, which can monitor skin temperature in real time. It can be used to test the contact condition between skin and RF electrode, also can be used to test whether cooling source offers the reasonable cooling temperature, meanwhile, to ensure the dose control in the course of treatment. The specific skin temperature monitor could be one temperature sensor or several temperature sensors, which used to monitor the temperature of skin surface, it may be thermistor element. The temperature sensor inside the forepart of the RF electrode, or embed in RF electrodes, or thermally isolated from thermal conductive element.

Cooling system is working before treatment. The cooling system will operate for 10-60 s. System judge the contact of electrode with skin based on received skin temperature from temperature sensor. For example, the cooling temperature set at 20° C., running the cooling system for 20 s, the detected skin temperature is 25° C., or activate the cooling device for 40 s, the detected skin temperature is 23° C., then we can affirm the cooling system is normal, and contact with skin well. When the treatment handpiece comprises multiple temperature sensors, after starting the cooling system, cooling temperature of temperature sensors will be supervised. The cooling system is considered as in normal condition on the condition that temperature checked by different temperature sensors is the same or with difference ±1° C., and in a good contact with skin.

RF electrode can use flexible printed circuit board or hard electrode materials as the electrodes. The size of the RF electrodes is variety, specific as strip electrode, lattice RF electrode, etc.

Treatment applicator can use bipolar RF, unipolar RF and combination of unipolar and bipolar. Unipolar RF has features of deep penetration and scattered energy. Bipolar RF has features of focused energy and shallow penetration.

The length of peripheral size of treatment electrode at longitudinal direction to the vaginal orifice is 1 cm-2.5 cm, the length of the cover angle transverse direction is 15°-90°, it's specific size could be 0.5 cm-3 cm, when the lateral size covered angle over 30°, in order to make sure the comfort and security during the treatment, it will need a arc electrode with 3 cm curvature.

The shape of RF electrode can be variety, strip unipolar/bipolar RF, lattice unipolar/bipolar electrode, strip and lattice combined bipolar electrode, and so on.

Due to the treatment of vaginal area involves serious health and safety problems, this equipment adopt one-time plug head, to avoid cross infection caused by improper disinfection, improve the safety and reliability. At the same time, in order to avoid irregularities use, to avoid supplies disinfection may use repeatedly, it had an ID chip in the one-time plug head. After connect the treatment handle and one-time head plug, start the main engine, the equipment can recognize plug head usage. A variety of restrictions way, such as set consumables does not work within 2 hours, after the initial connection to main engine communication, or set material can only be connected to the main engine one time. Beyond the limit requirements, Device does not perform the work.

As shown in FIG. 1, the machine compose by the top of the main engine 1, connect through the link device 2 then it's connected to the tail of the hand piece 3, Negative plate 4 and the main engine connected to each other, form a circuits with the RF positive of hand piece 3, in the process of treatment.

As shown in FIG. 1, the main engine 1 have a RF power supply, cooling device, display, and their control circuit, and the RF power supply is a continuous output power. Connection device 2 contains a RF signal lines, temperature sensor cable, water-cooling system transmission device, recognition of the hand piece 3 chip cable lights, etc. There is a one-time plug fixture in the front of hand piece 3, it provide cooling source and RF energy to the treatment plug.

Figure 10:
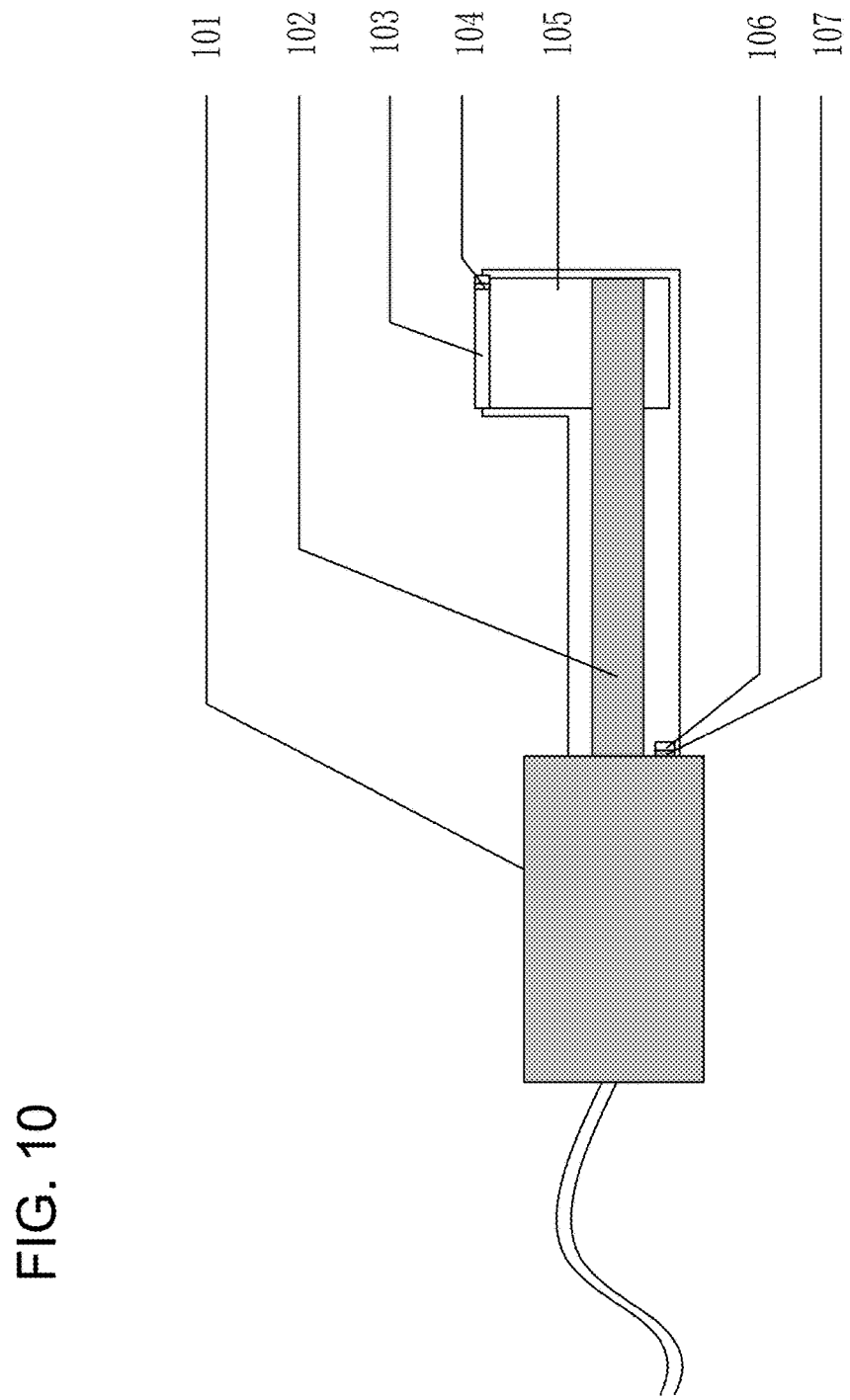
FIG. 10 is a schematic diagram of a hand piece structure schematic diagram of RF treatment device for vaginal orifice tightening.

As shown in FIG. 10, the top of the hand piece connect with the one-time plug by jam method. Hand piece 3 comprises handle and plug part, The shell is fixed with card slot. The handle comprises the functional component, such as carrying parts 101, identifying chips 104, thermal conductive device 105, recognition chip and the RF signal source interface female end 106. Described cooling water pipe 102 provide 16-28° C. cooling water to the hand piece plug, transfer the heat to therapeutic electrode 103 through thermal conductive element 105, and provide cooling to the skin.

The described identification chip and the RF signal interface box end use the point contact connection mode or socket connection mode, this is a component with multiple connection or jack, its main function are transmit the RF signal, identification chip signal transmission, the temperature sensor signal transmission.

The described cooling water pipe is cylindrical water cycle mode design, the inlet pipe and outlet pipe are both concentric circles, bulkhead is in the Middle, and convert water pipe at the end of the cooling water pipe and the junction of heat conduction device, outlet pipe, inlet pipe, cooling water pipe and the middle bulkhead form Into the water pipe, the bulkhead is hollow serve as pressure pipe road.

The described thermal conductivity element is rectangle or cubes shape formed by high thermal conductive materials, we dig a cylindrical hole internal and connected it to the cooling water pipe.

Figure 11:
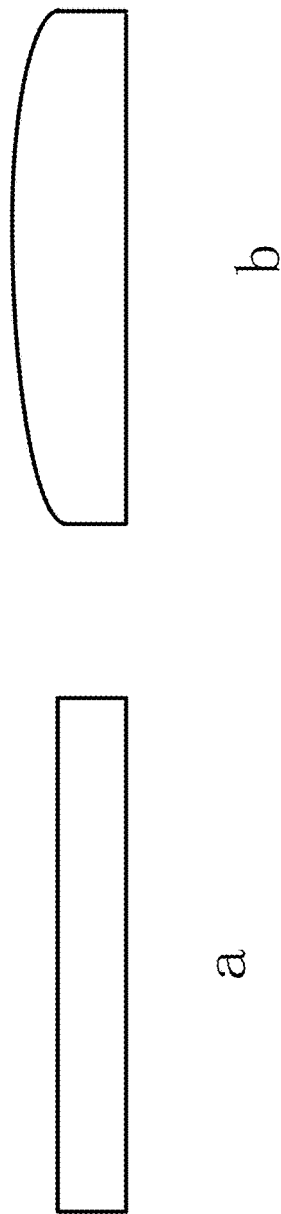
FIG. 11 is different RF electrodes section views of RF treatment device for vaginal orifice tightening.

As shown in FIG. 11, treating plug RF electrode parts contact with the skin can be smooth and flat, or have certain curvature of curve.

As shown in FIG. 12, linear shape unipolar RF electrode, the specific FIG. 12 for strip RF electrodes is one.

Figure 13:
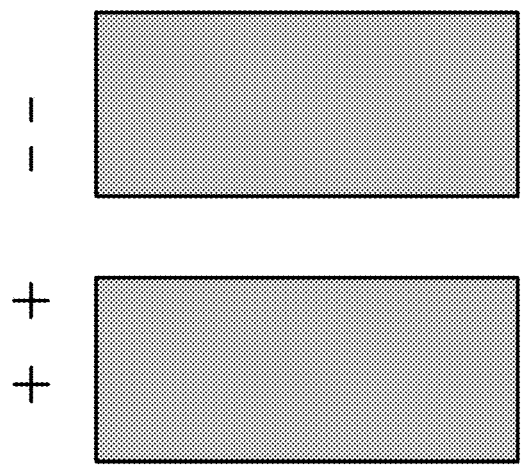
FIG. 13 is the bar shape electrode(bipolar RF) schematic diagram of RF treatment device for vaginal tightening.

As shown in FIG. 13, linear Bipolar electrode, specific FIG. 13 is one pair of linear RF electrod.

As shown in FIG. 14, linear shape unipolar RF electrode, the specific FIG. 14 for strip RF electrodes is two or more than two.

As shown in FIG. 15, linear Bipolar electrode, RF positive and negative are both bipolar linear electrodes.

As shown in FIG. 16, linear bipolar RF electrode, one pole of the RF is linear, and another pole is electrode lines surround around the periphery.

As shown in FIG. 17, RF electrode is in fractional and unipolar.

As shown in FIG. 18 is fractional RF electrode, positive and negative polar of the RF arrangement are cross arranged.

As shown in FIG. 19, RF electrode is fractional bipolar electrode, one polar of the RF is fractional, and another polar of the RF is linear that surrounding at outside.

Working mechanisms according to some embodiments:

Connect treatment applicator (negative plate, foot switch, disposal treatment plug, start, dosage setting and cut-off temperature) and run validation procedures(respective validation of applicator, negative plate, foot switch to the main engine, connection validation between treatment plug ad applicator, authorization validation of treatment plug). Insert plug into vagina to for contacting validation and skin cooling validation. After validation, start the treatment.

Specific Implementation Modalities

Here by a specific implementation explains the concrete implementation of the disclosure, people who familiar with the technology can easily understand other advantages of the disclosure and its efficacy by the content revealed in this manual.

The structure, scale, size, etc. of attached picture in this specification only used to reveal the manual content, help those familiar with the technology to understand and read, not restrict qualification of this disclosure can be implemented, so they don't have any technology essence, any structural modification, proportional adjustment or size changing, shall not affect this disclosure or its achieve purpose, it will remain in the scope of reveals technical content of this disclosure. At the same time, the terms referenced in this manual, such as "up", "down", "left", "right", "middle" and "a" and other terms, also use to narrative and clear, not to limit the scope of the disclosure can be implemented; change or adjust of relative relationship, with the condition of no substantial changes of the technical content , will also be regarded as the implement category of this disclosure.

Figure 20:
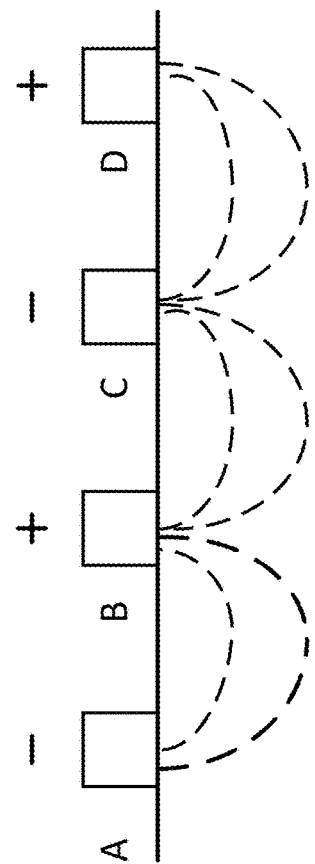
FIG. 20 is the electric effect schematic diagram of frictional RF therapy apparatus with the existing arrangement of RF electrode structure.

Fractional RF in the existing treatment technology treat the skin by let the anode and cathode RF electrode current breakover go through the skin tissue, commonly the RF electrode on therapeutic apparatus is array type method, as shown in FIG. 20, shows the RF electrode arrangement diagram of the existing frictional RF therapy apparatus. As shown, in this Figure marked out the current flow distribution between RF electrodes, because the electric charge will moving along in the direction of least resistance, so in the this Figure, between negative electrode A and positive D, because it has the opposite electrode B or C, so the current flow of electrode A flow into B not D. In addition, electrode B provides current path to electrode C and electrode A at the same time, so the current pass through B is current overlap of electrode A and electrode C.

As such, during the treatment calculate by the energy formula: $Q=I^2*R*t$, whereby I is the current size, R for the skin impedance (as resistance), t is through the current of time. And set the positive electrode B and D by the method of potential, the current is I, the current at place A is 0.5 times I, the current at place C is 1.5 times I.

Figure 22:
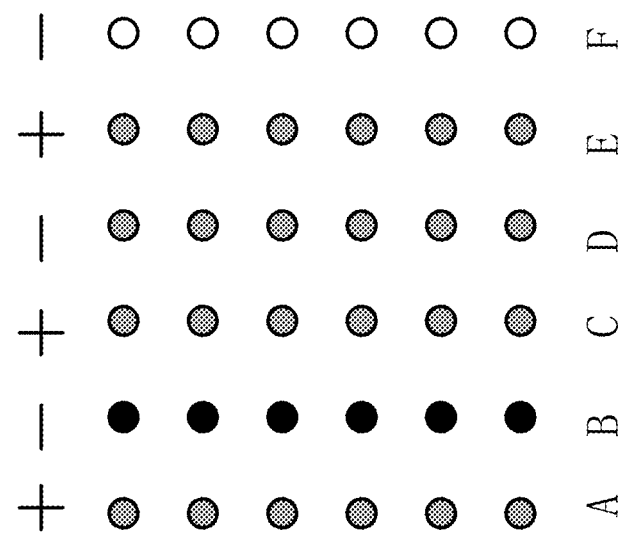
FIG. 22 illustrates the RF electrode array under current.
Figure 21:
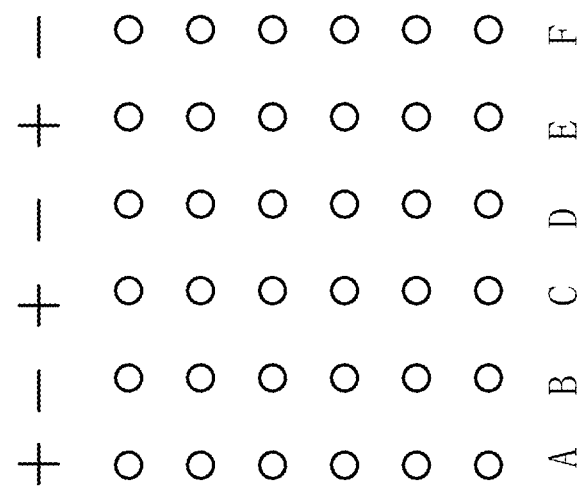
FIG. 21 is the structure diagram of an RF electrode array.

In addition, the RF configuration in the existing RF frictional multiple anode and cathode in the RF therapy apparatus have following methods, it is also connected by the abovementioned circuit structure, only changed the method of RF electrode configuration. As shown in FIG. 21, it shows one of the RF electrode arrangement structure in the existing technology, among them, the positive cathode are matrix, set the anode current as I (namely the ACE electrode current are I), the B electrode current is 1.5 I, the D electrode current is I, F electrode current is 0.5 I. So, B electrode is 3 times of F electrode, electrode current density for ACDE electrode is 1.5 times during the actual use (see FIG. 22).

Figure 24:
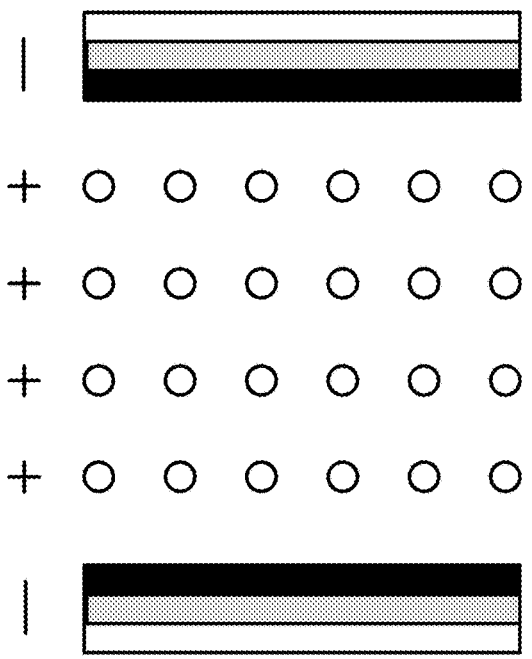
FIG. 24 illustrates the RF electrode array under current.
Figure 23:
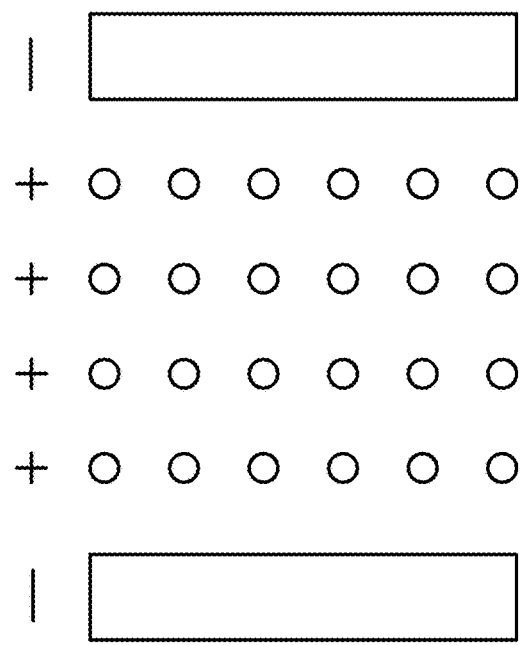
FIG. 23 is the structure diagram of another RF electrode array.

Furthermore, as shown in FIG. 23, it shows another arrangement way of frictional RF electrode diagram, the middle dot matrix are positive, the edge of the long strip are negative, corresponding, FIG. 24 is the frictional RF electrode current sketch after heating, we can see from FIG. 24, the energy distribution on RF in the middle of the positive electrode is relatively uniform, but the energy distribution is tilted at the edge of the RF cathode electrodes.

In conclusion, in the existing RF treatment, the treatment energy of RF energy emission treatment operation methods is significant difference, resulting in uneven treatment dose.

IMPLEMENTATION EXAMPLE 1

Figure 25:
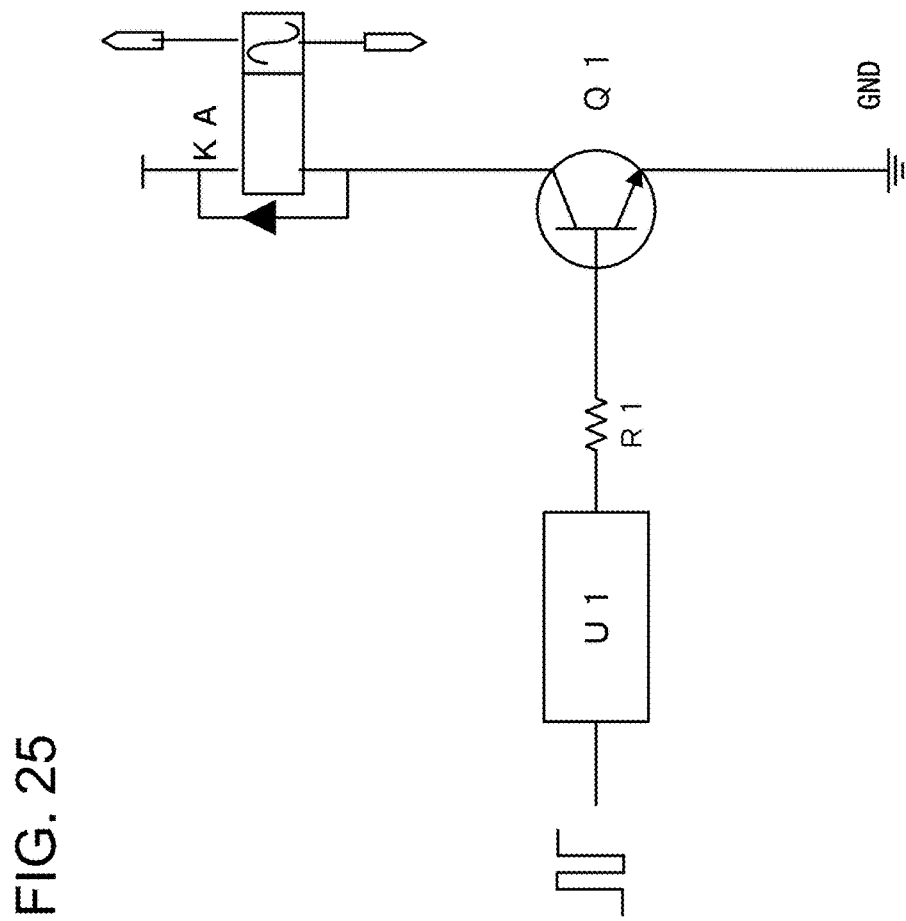
FIG. 25 is one of the RF electrodes driving circuit working principle diagram according to some embodiments.

In order to solve the abovementioned problems, the disclosure provides a RF electrode driving circuit, as shown in FIG. 25, is the principle diagram of the RF driver circuit, RF electrode driving circuit including optical coupler U1, transistor Q1 and relay KA, the transistor Q1 base electrode connect to the abovementioned optical coupler U1 through resistor R1, the abovementioned collector of the transistor Q1 connect to the relay KA, the emitter electrode of the transistor Q1 connect to the output.

In the abovementioned RF electrode driving circuit, the optical coupler U1 input used to receive incentive source (for example, the high level), to trigger the conduction between transistor Q1 collector and emitter, thus drive the coil driver on the relay to adsorbing the often open end, achieve the goal of closed or disconnected the driving switch.

Figure 26:
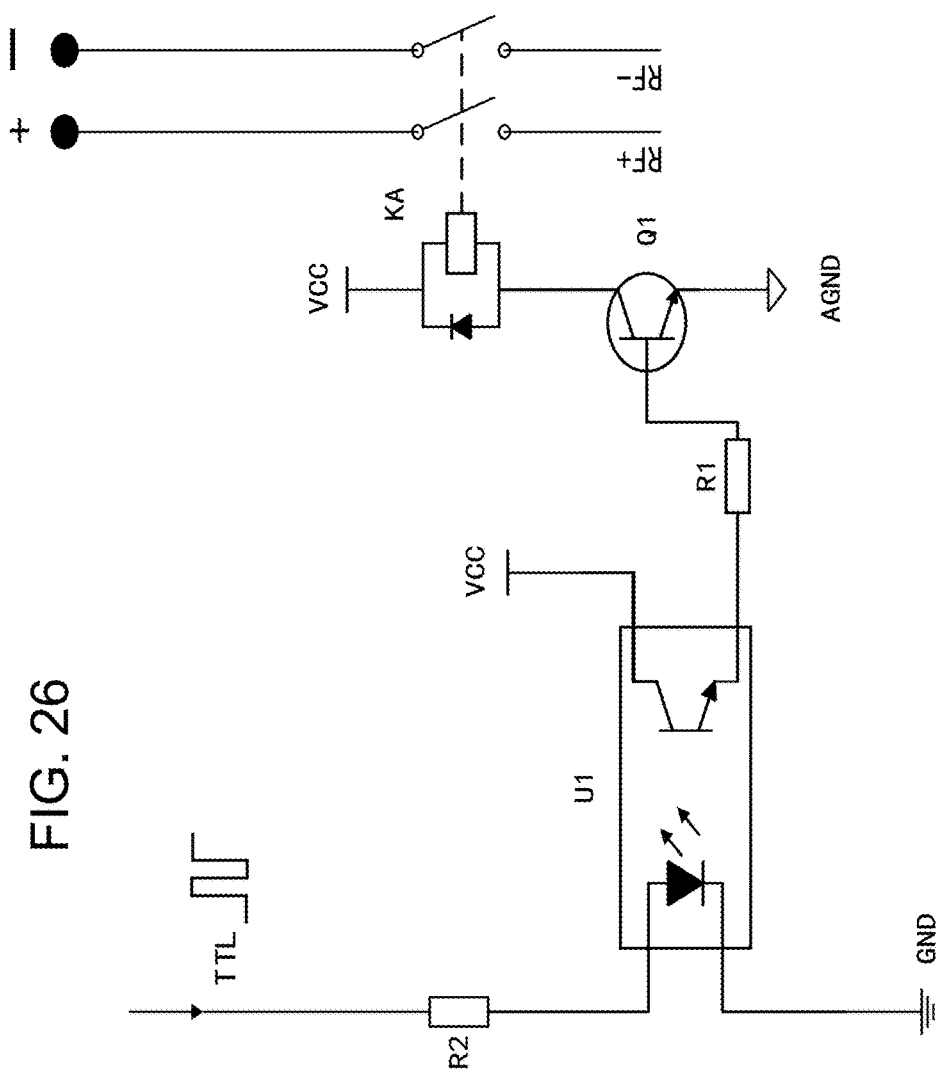
FIG. 26 is the circuit diagram in the cases of RF electrode driving circuit as described.
Figure 27:
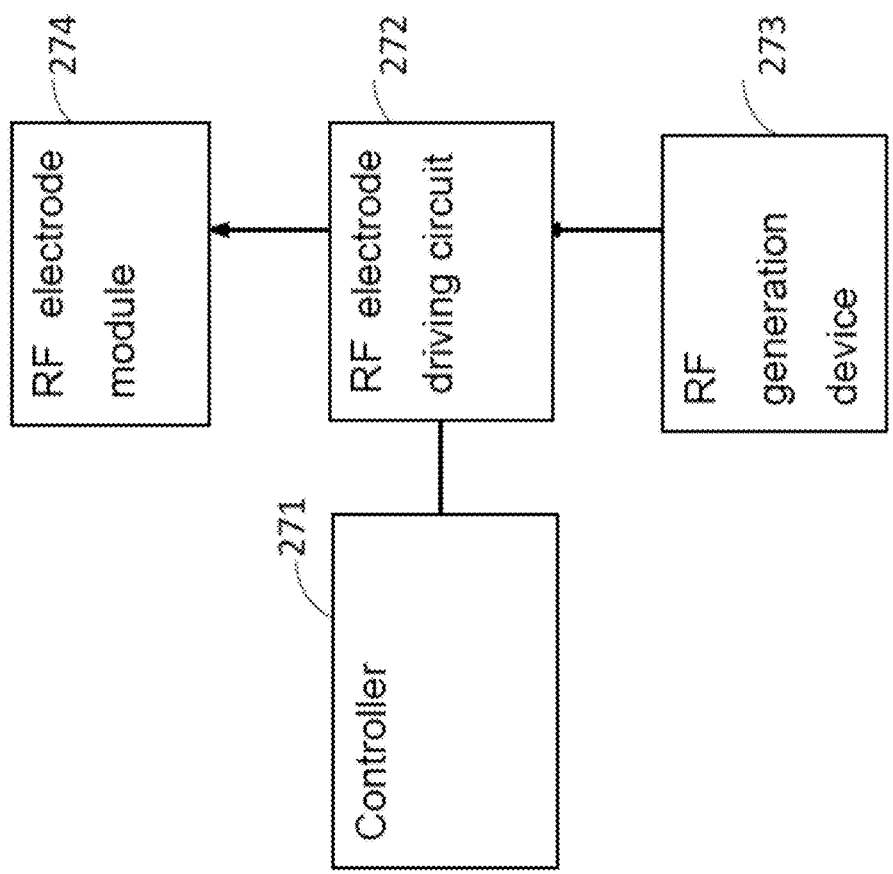
FIG. 27 is the principle diagram of a RF output device according to some embodiments.

Specifically, as shown in FIG. 26, it shows a method to implement the abovementioned RF electrode driving circuit diagram, as shown in the Figure, the abovementioned optical coupler U1 connect to resistor R2 through the anode of its input, the cathode of the input of optical coupler U1 connect the ground, and one output end of the abovementioned optical coupler U1 connect to power supply VCC, another end connect the one end of the resistor R1; the other end of the resistor R1 connect to the base of transistor Q1; the collector of transistor Q1 connect to the end of the coil on relay KA, another end of the coil in the abovementioned relay KA connect to the power supply KA VCC, the emitter electrode on the abovementioned transistor Q1 connect to the output (or equipotential).

In practical circuit, the abovementioned RF electrode driving circuit can be mounting between the RF source and RF electrode, to drive the RF electrode and the source of the RF breakover or disconnected. Among them, the abovementioned resistance R2 can limit the current, when the excitation source is connected or arrival, to make the optical coupler become breakover, then increases current in resistor R1, increases voltage in the base electrode of transistor, so the transistor will become conduction, then the relay coil have electricity and adsorption the often open end, to make RF electrode connected to the RF source breakover. Here set a photoelectric coupler aimed to preventing any affect of the excitation source will not cause by accident from RF electrode or RF source, so as to guarantee the safety of the circuit.

Understanding, that it will also work, if it driven directly by the relay and transistor radiofrequency electrode, only it's lack of certain safety. In addition, should understand the transistor is NPN, used as connection between optical coupler and the relay. If there is anything we are not mention above, all because the connection method is understood by those skilled in the art, so there is no need to specify here.

IMPLEMENTATION EXAMPLE 2

Furthermore, compare to the RF electrode working of the existing RF treatment, the abovementioned RF electrode driving circuit 272 can be designed into different RF electrode array, to maintain the electric current as the same, prevent the situation of the uneven current distribution.

Specifically, As shown in FIG. 4, shows the principle diagram of a RF output device, including: RF electrode module 274, with multiple sets of RF electrodes; RF generator 273, used to output multiple number RF source corresponding to the abovementioned number of RF electrode, and the abovementioned multiple RF sources connect to multiple groups of RF electrodes by multiple RF electrode driving circuit 272 in turn corresponding; controller 271 connect to the abovementioned RF electrode driving circuit 272 to output the RF excitation source as preset frequency, then trigger the abovementioned RF electrode driving circuit 272 breakover, driving the abovementioned multiple groups of RF electrode with multiple RF source circulating breakover to work in turn.

Specifically, there are multiple sets of RF electrodes in the abovementioned RF electrode module 274 are regularly arranged in frictional, and each group of RF electrode including anode RF and cathode RF electrode, it connect to the ends of double single throw switch of the relay in the abovementioned RF electrodes driving circuit 272, respectively. The sets of RF electrode match with multiple RF electrode driving circuit 272; Accordingly, each RF in the abovementioned multiple RF source connect to another end of double single throw switch of the relay in the abovementioned RF electrode driving circuit 272, respectively.

Specifically, the abovementioned controller 271 can be a single chip microcomputer, it trigger multiple RF electrode driving circuit breakover 272 in turn by certain output frequency excitation source, so as to make connection between RF source and RF electrode breakover, which is connected by RF electrode driving circuit breakover 272.

Figure 28:
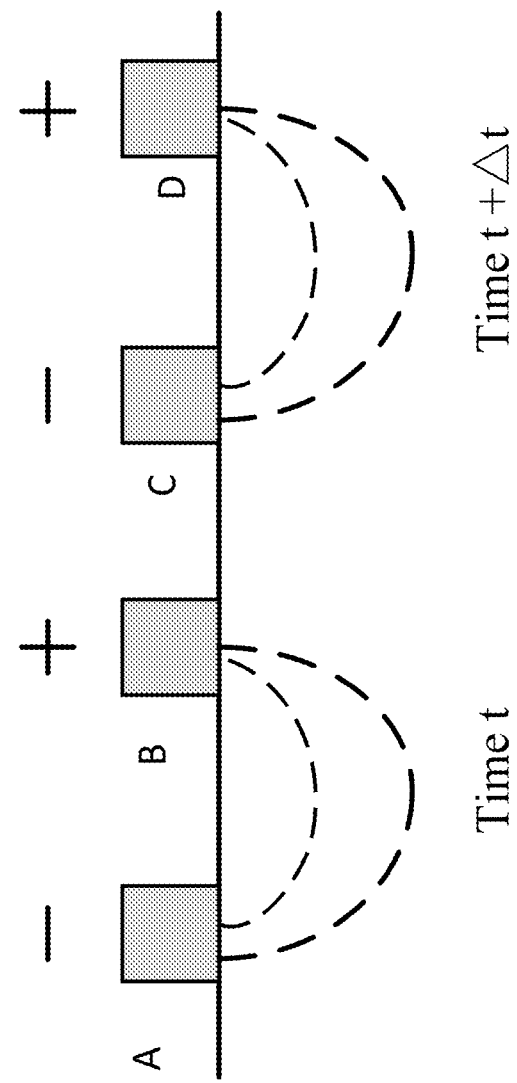
FIG. 28 is the actual use effect diagram of RF output device with two groups RF electrodes.
Figure 29:
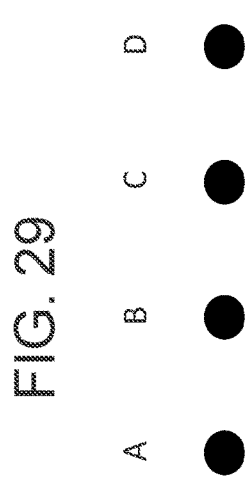
FIG. 29 is the diagram of current distribution effect of RF output device with two groups RF electrodes.

For example, as shown in FIGS. 28 and 29, is the effect diagram of the two groups RF electrode in the abovementioned RF output device in actual use, respectively, A and B as a pair of radio frequency (RF) electrodes, C and D is a pair of RF electrode. During the treatment, according to the control of the excitation frequency, in t time, RF electrodes A and B put through the positive and negative electrodes of RF source at the same time, at t+Δt time, RF electrodes C and D put through the positive and negative electrodes of RF source at the same time (as shown in FIG. 28). So, if the current size is I, then the current flows pass through electrode ABCD are equal (as shown in FIG. 29), namely uniform treatment dose, little side effect and obtain a uniform treatment.

Furthermore, normally we need to treatment the whole surface quickly, may be the launch time for one specific RF anode/cathode group is controlled within 0.5 s, more concretely maybe 0.2 s-0.3 s.

Figure 30:
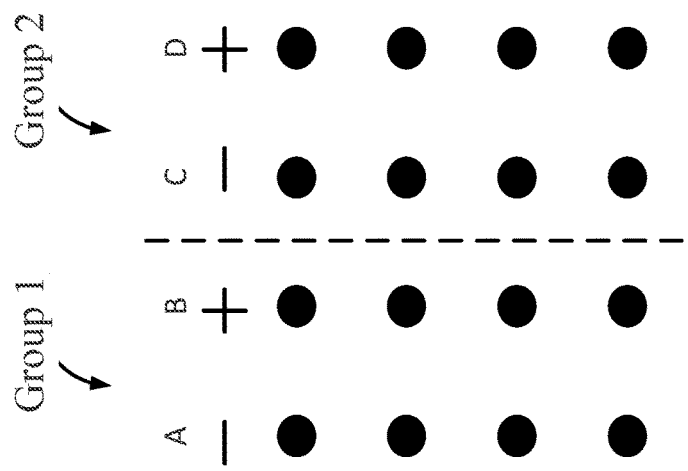
FIG. 30 is a square RF electrode arrangement diagram.

And furthermore, it can also expand the described one set of RF electrode into one or multiple RF electrode array, thus use the abovementioned RF electrode module 274 to lay out all kinds of RF treatment electrode shape, as shown in FIG. 30, which shows a square RF electrode arrangement diagram, including 2 groups of RF electrodes: group 1 and group1 2, respectively. In actual treatment, group 1 and group 2 circular breakover in turn, it not only satisfy the purpose of quick treatment for the large area, but also ensure each RF electrode are at the same current.

Figure 31:
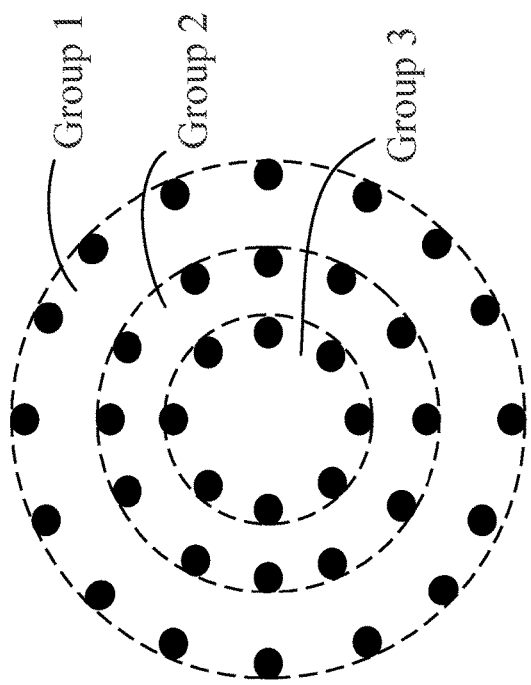
FIG. 31 is a circle RF electrode arrangement diagram.

Or, FIG. 31, shows a round RF arrangement diagram, which include three groups of RF electrodes: group 1, group 2 and group 3, respectively; in the actual treatment, work circulating conduction in group 1, group 2 and group 3, it not only satisfy quick treatment of large area, but also ensure each RF electrodes are at the same current.

In conclusion, this disclosure use RF electrode driving circuit 272 to drive the breakover of RF electrode and RF source separately, at the same time, conFigure the RF electrodes treatment by multiple sets of RF electrode cyclic breakover, ensure uniform current distribution between each RF electrode groups, solve the problem of uneven current distribution during the treatment of the existing RF electrode treatment perfectly. Therefore, this disclosure overcome a lot of shortcomings effectively in the existing technology and has high industrial value.

In some embodiments, the mentioned optical coupler connect to one end of the second resistors by its input terminal, another end of the second resistors connect to the controller, optical coupler connect to ground by its another input terminal, optical coupler connect to power source by one of its output terminal, optical coupler connect to another terminal of the first resistors by its another output terminal, another terminal of the first resistors connect to the transistor base electrode, the collector electrode of the transistor connect to the upper end of the coil on relay, the another upper end of the coil on relay connect to the power source, the normally closed and open switch on relay is connect to each one group of RF electrode and RF source respectively.

In some embodiments, the RF electrodes include a couple of positive and negative RF electrodes. In some embodiments, the RF electrodes have a pair of positive and negative RF electrode array.

Refer terms describes in this manual, such as "an implementation example", "some implementation examples ," " demonstrations," "specific demonstrations," "some of the examples," etc., indicate specific features, structure, material or characteristics in the implementation example or demonstrations are involved in at least one implementation example or demonstrations of this disclosure. In this instruction, illustrative expression of the above terms does not always indicate the same implementation example or demonstrations. Furthermore, specific features, structure, material or characteristics are allowed to combine in one or multiple implementation example or demonstrations.

Although specific embodiments have been described above in detail, the description is merely for purposes of illustration. It should be appreciated, therefore, that many aspects described above are not intended as required or essential elements unless explicitly stated otherwise. Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A radio-frequency (RF) apparatus configured for vaginal treatment, the apparatus comprising:
   a main engine;
   a connection device;
   an applicator; and
   a negative electrode plate,
   wherein:
      the applicator comprises a hand-held component and a treatment plug,
      the main engine is coupled with the hand-held component through a connector,
      the treatment plug has multiple RF electrodes disposed thereover; and
      the treatment plug comprises one or more identification chips disposed inside the treatment plug.

2. The apparatus of claim 1, wherein the treatment plug has a size substantially similar to a size of a target, wherein the size of the treatment plug is configured to allow treatment of the target without substantial movement of the plug, and wherein the apparatus is configured for vaginal wall tightening.

3. The apparatus of claim 1, wherein the hand-held component comprises a handle and a cooling circuit, wherein the cooling circuit is disposed in the handle and has an extension portion that extends from the handle.

4. The apparatus of claim 3, wherein the treatment plug comprises a plurality of heat conductive elements and a temperature sensor, wherein the multiple RF electrodes are wrapped within an outermost layer of the treatment plug, wherein the plurality of heat conductive elements are disposed inward of the RF electrodes, wherein the extension portion of the cooling circuit is disposed inward of the heat conductive elements; and wherein the temperature sensor is disposed among the RF electrodes.

5. The apparatus of claim 4, wherein the temperature sensor is configured as one of the following: (A) inserted in the RF electrodes, (B) attached to an upper surface of the RF electrodes, or (C) attached to a lower surface of the RF electrodes, wherein the temperature sensor is thermal-isolated from the plurality of heat conductive elements, and wherein the temperature sensor comprises one or more sensing elements.

6. The apparatus of claim 1, wherein the treatment plug has a diameter of about 2.5 cm- 3.75 cm and a length of about 7 cm- 15 cm.

7. The apparatus of claim 1, wherein the RF electrodes have a pattern of one of round, bar, linear, ring, polygon, irregular arc, or a combination thereof, and account for about 5%-80% of an outer wall area of the treatment plug.

8. The apparatus of claim 1, wherein the RF electrodes have shapes of one of a rectangular shape, a bar shape, or a circular shape.

9. A radio-frequency (RF) apparatus configured for vaginal treatment, the apparatus comprising:
   a main engine;
   a connection device;
   an applicator; and
   a negative electrode plate,
   wherein:
      the applicator comprises a hand-held component and a treatment plug,
      the main engine is coupled with the hand-held component through a connector,
      the treatment plug has multiple RF electrodes disposed thereover; and
      the RF electrodes are in a circular distribution with a specified inclination or vertical angle.

10. The apparatus of claim 1, wherein the RF electrodes are arranged in at least one of a linear unipolar or bipolar distribution, forming a current loop within a local small area.

11. The apparatus of claim 1, wherein the RF electrodes are arranged in a bipolar distribution having one pole located at an inner ring and another pole located at an outer ring; or in a fractional bipolar distribution with both poles cross distributed, and wherein a ratio between numbers or areas of both poles is no more than two.

12. The apparatus of claim 1, wherein a cross section of an end portion of the treatment plug is larger than a remaining portion of the treatment plug, wherein the multiple RF electrodes are distributed at the end portion of the treatment plug, and wherein the apparatus is configured for vaginal orifice tightening.

13. The apparatus of claim 12, wherein the RF electrodes have a pattern of one of round, bar, linear, ring, polygon, irregular arc, or a combination thereof.

14. The apparatus of claim 13, wherein the RF electrodes are bar-shaped unipolar RF electrodes or linear RF electrodes.

15. The apparatus of claim 13, wherein the RF electrodes are bar-shaped bipolar electrodes, linear bipolar RF electrodes, linear bipolar RF electrodes with one pole having linear shape and another pole surrounded by the bar-shaped electrodes, or fractional-shaped unipolar RF electrodes.

16. A radio-frequency (RF) apparatus configured for vaginal treatment, the apparatus comprising:
   a main engine;
   a connection device;
   an applicator; and
   a negative electrode plate,
   wherein:

the applicator comprises a hand-held component and a treatment plug, the main engine is coupled with the hand-held component through a connector, the treatment plug has multiple RF electrodes disposed thereover; and the connector comprises one of a card slot or a thread.

17. The apparatus of claim 1, wherein the hand-held component comprises a grip portion including a handle portion, the apparatus further comprising:

an identification chip, an RF signal source interface male end, and a cooling water pipe portion, the handle portion having a top end connect to the identification chip and an RF signal source interface male end, wherein:

the identification chip and an RF signal source interface female end connect to an identification chip male end, one end of the cooling water pipe portion is connected to the handle portion top end, and another end of the cooling water pipe portion is connected to a thermal conductive element.

18. The apparatus of claim 1, further comprising an RF electrode driving circuit including an optical coupler, a transistor, and a relay, the transistor having a base electrode, a collector electrode, and an emitter electrode coupled to the optical coupler, the relay, and an output source, respectively.

19. The apparatus of claim 18, wherein the optical coupler is coupled to one end of a first resistor, an input of the optical coupler coupled to ground, an output of optical coupler coupled to a power source, another end of the optical coupler coupled to one end of a second resistor, and another end of the second resistor coupled to the transistor base electrode, wherein the first resistor is coupled to the power source by another end, wherein the transistor is NPN type, the driving circuit further comprising a controller configured to generate a preset output RF frequency for an excitation source to trigger the driving circuit, to thereby drive the multiple RF electrodes and multiple RF sources.

* * * * *